United States Patent
Lilienfeld

(10) Patent No.: US 7,197,911 B1
(45) Date of Patent: Apr. 3, 2007

(54) METHODS AND APPARATUS FOR MECHANICAL RESONANCE MONITORING A MASS CONCENTRATION OF PARTICULATE MATTER

(75) Inventor: Pedro Lilienfeld, Lexington, MA (US)

(73) Assignee: Thermo Electron Corporation, Waltham, MA (US)

( * ) Notice: Subject to any disclaimer, the term of this patent is extended or adjusted under 35 U.S.C. 154(b) by 0 days.

(21) Appl. No.: 11/029,285

(22) Filed: Jan. 5, 2005

Related U.S. Application Data

(63) Continuation-in-part of application No. 10/837,393, filed on Apr. 29, 2004, now Pat. No. 7,111,496.

(51) Int. Cl.
*G01N 37/00* (2006.01)

(52) U.S. Cl. .................... 73/28.01; 73/24.03

(58) Field of Classification Search .......... 73/28.01, 73/23.31, 24.01, 24.02, 24.03, 24.04, 24.05, 73/24.06, 23.36
See application file for complete search history.

(56) References Cited

U.S. PATENT DOCUMENTS 3,569,825 A * 3/1971 Lilienfeld .............. 324/464
3,879,992 A * 4/1975 Bartera ................. 73/24.01
4,446,720 A * 5/1984 Sinclair ................. 73/24.06
5,349,844 A * 9/1994 Lilienfeld .............. 73/28.01
6,167,747 B1 * 1/2001 Koch et al. ............ 73/19.03

FOREIGN PATENT DOCUMENTS

EP 1059521 * 12/2000

* cited by examiner

*Primary Examiner*—Helen Kwok
(74) *Attorney, Agent, or Firm*—Chapin IP Law, LLC; Barry W. Chapin, Esq.

(57) ABSTRACT

A particulate mass monitor includes a controller that monitors a change in a resonant oscillation frequency of a taut metallic membrane, as caused by deposition of the particulate matter on the metallic membrane. The metallic membrane, such as a foil or metallized plastic film, is substantially mechanically stable under tension. Application of a tension to the periphery of the metallic membrane generates a substantially constant tension within the membrane, thereby allowing the particulate mass monitor to detect a particulate mass concentration of the air sample with a relatively high degree of accuracy. Additionally, the particulate mass monitor includes a membrane transporter that automatically advances the metallic membrane within the particulate mass monitor. The membrane transporter minimizes the necessity for manual replacement of the metallic membrane over time and allowing long term, unattended operation of the particulate mass monitor.

33 Claims, 10 Drawing Sheets

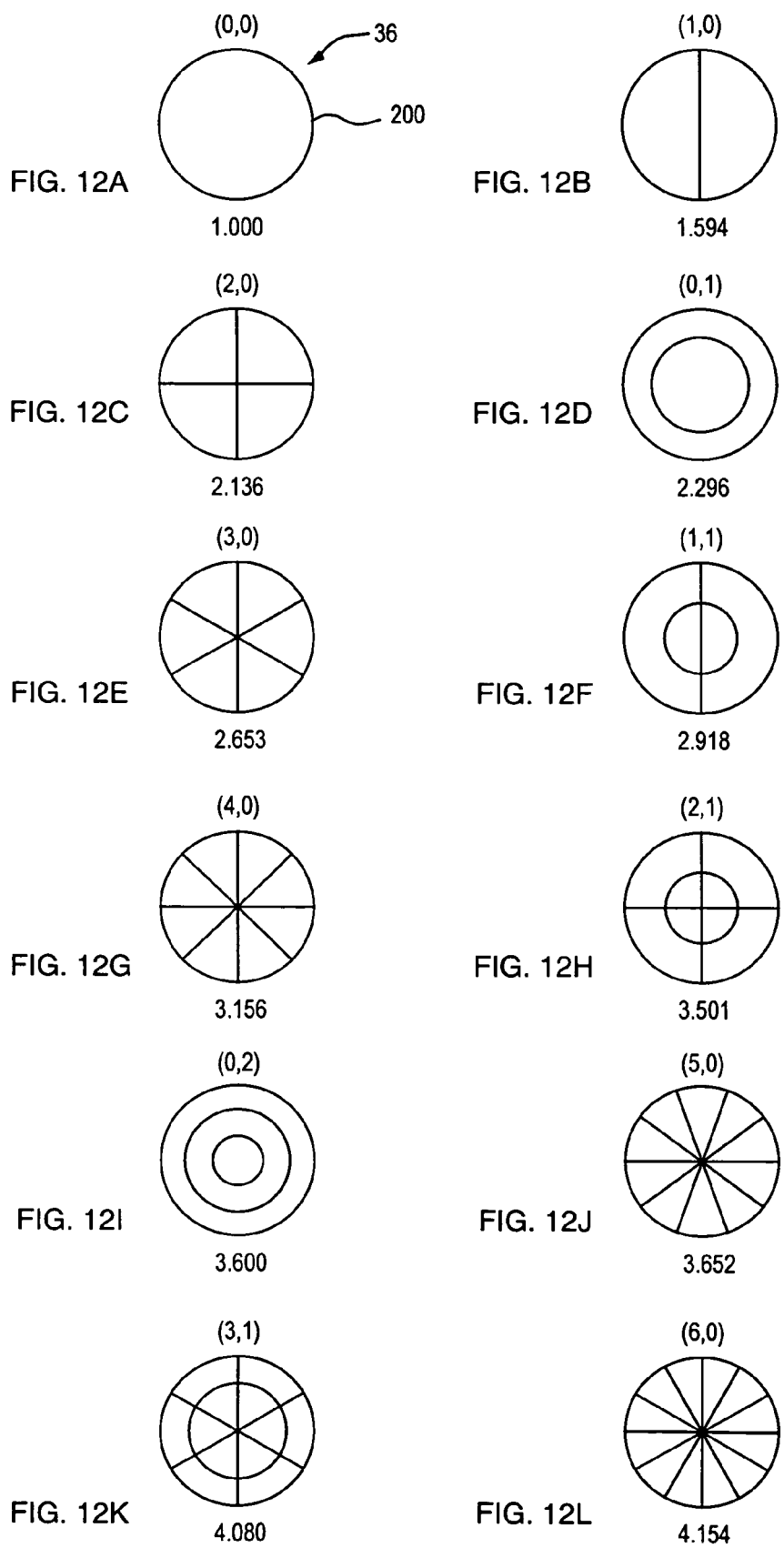

METHODS AND APPARATUS FOR MECHANICAL RESONANCE MONITORING A MASS CONCENTRATION OF PARTICULATE MATTER

RELATED APPLICATIONS

This application is a continuation-in-part of U.S. Utility application Ser. No. 10/837,393, entitled "METHODS AND APPARATUS FOR MONITORING A MASS CONCENTRATION OF PARTICULATE MATTER" filed Apr. 29, 2004 now U.S. Pat. No. 7,111,496 and assigned to the same assignee, the entire teachings of which are hereby incorporated by reference.

FIELD OF THE INVENTION

Embodiments of the present invention relate generally to a system and method for measuring and monitoring the mass concentration of airborne particles.

BACKGROUND

Ambient air quality affects the health of people breathing the ambient air. The lower the air quality, the greater the risk for health-related problems induced by the ambient air. Conventional particulate matter monitors measure the mass concentration of particulate matter within ambient air, gases, or other fluids to detect the quality of the ambient air or gaseous fluid. A conventional particulate matter monitoring device can provide a warning to a user when the device detects a relatively low air quality (e.g., a relatively large particulate mass concentration within the air) or a decrease in the ambient air quality based upon an increase in particulate mass concentration measured over a specific time period.

Certain sensing techniques, such as in mechanical resonance sensing, detect the particulate mass concentration of an air sample. For example, a conventional particulate matter monitor includes a collector that collects particulate matter within an air sample and that detects the mass of the particulate matter based upon the mass-spring principle. If the collector is part of a mechanically resonating system, the natural resonance frequency of the system decreases as the collected mass of the particulate matter increases. The general equation governing this behavior is:

$$\Delta m = m_0[(f_0/f_f)^2 - 1]$$

where $\Delta m$ is the mass increment of collected particulate matter, $m_0$ is the total initial mass of the resonating system, and $f_0$ and $f_f$ are the initial (before particle collection) and final (after particle collection) resonance frequencies of the oscillating system (e.g., of the collector).

One type of particulate matter monitor utilizing mechanical resonance sensing includes a quartz crystal microbalance. Conventional quartz crystal microbalances have a thin piezoelectric quartz crystal sandwiched between two metal electrodes. The conventional quartz crystal microbalances collect particulate matter on the surface of the quartz crystal from an air sample using either electrostatic precipitation or jet-to-plate impaction. As the piezoelectric quartz crystal receives the particulate matter, the quartz crystal microbalance provides an alternating electric field to the piezoelectric quartz crystal, causing the quartz crystal to generate a shear-induced acoustic wave. Changes in the mass of the quartz crystal, as caused by deposition of particulate matter, affect the frequency of the wave. In such a configuration, the quartz crystal microbalance allows for detection of and quantification of relatively small masses of particulate matter within an air sample.

Another type of particulate matter monitor utilizing mechanical resonance sensing includes a tapered-element oscillating microbalance (TEOM). In a conventional TEOM, a filter cartridge attached to a tapered element of the TEOM receives an air or gas sample pumped at a known flow rate. The TEOM produces an alternating voltage signal that oscillates the tapered element at the resonant frequency of the tapered element/filter cartridge combination. As the filter cartridge, attached to the tapered element, removes particulate matter from the air or gas sample, the mass change of the tapered element causes a frequency shift in the resonant frequency of the tapered element. The frequency shift of the signal relates to the mass accumulated by the tapered element/filter cartridge combination of the TEOM and relates to the amount of particulate matter within the air sample.

Another type of particulate matter monitor utilizing mechanical resonance sensing includes a resonant taut filter membrane sensing system. The conventional taut filter membrane sensing system includes an annular piezoelectric driver to impart an oscillation to a taut filter and a miniature microphone to detect the resonance frequency of the filter. The taut filter membrane sensing system detects the mass of particulate matter collected on the taut filter by oscillating the filter, thereby causing the filter to resonate at its natural mechanical resonant oscillation frequency (e.g., characteristic fundamental frequency or fundamental mode). As particulates within an air sample accumulate on the filter, the resonant frequency of the filter's oscillation decreases due to the additional particulate mass. The taut filter membrane sensing system calculates the mass concentration of airborne particulates within the air sample based upon the decrease in the natural resonant frequency of the taut filter.

Additionally, the conventional taut filter membrane sensing system is configured to oscillate the taut filter at higher, non-harmonic modes related to the fundamental mode or characteristic fundamental frequency of the filter. As particulates within an air sample accumulate on the filter, the oscillation of the filter at the higher, non-harmonic modes decreases due to the additional particulate mass. By using the higher, non-harmonic modes to oscillate the taut filter, the resonant taut filter membrane sensing system allows for relatively sensitive measurements of particulate matter concentrations within an air sample, compared to measurements taken using fundamental mode oscillations.

SUMMARY

Conventional mechanisms and techniques that provide monitoring of airborne particulate mass concentration levels suffer from a variety of deficiencies.

As indicated above, one type of particulate matter monitor utilizing mechanical resonance sensing includes a quartz crystal microbalance. The conventional quartz crystal microbalances collect particulate matter on the surface of the quartz crystal from an air sample using either electrostatic precipitation or jet-to-plate impaction. However, because of the configuration of quartz crystal microbalances, the use of quartz crystal microbalances is typically constrained to laboratory use. For example, the relatively small total accumulated mass capacity of the quartz crystal requires frequent crystal cleaning or surface restoration. Such requirements for cleaning or resurfacing can be impractical to a user while in the field (e.g., away from the laboratory environment).

Also, another type of particulate matter monitor utilizing mechanical resonance sensing includes a tapered-element oscillating microbalance (TEOM). While the TEOM allows for ambient air monitoring of particulate matter, measurements made by the TEOM are susceptible to positional and vibrational effects. For stationary, fixed-point applications (e.g., within a laboratory) positioning or vibration of the TEOM minimally affects the measurements made by the TEOM. However, in relatively severe environments (e.g., blasting sites, coal mines, etc.) vibration of the TEOM can have a relatively substantial effect on the TEOM measurements. Additionally, over time, the filter cartridge attached to the tapered element receives a relatively large quantity of particulate matter. As such, due to particle volatilization and/or reception of moisture present within the air samples, the accuracy of the TEOM measurements can become compromised. Also, conventional TEOMs require routine manual replacement of the particle collection medium (i.e., the filter cartridge) of the tapered element thereby minimizing long term unattended operation.

Another type of particulate matter monitor utilizing mechanical resonance sensing includes a resonant taut filter membrane sensing system. The resonant taut filter membrane sensing system detects the mass of particulate matter collected on a taut filter by oscillating the taut filter to resonate at its natural mechanical resonant oscillation frequency. As particulates within an air sample accumulate on the filter, the resonant frequency of the filter's oscillation decreases due to the additional particulate mass. The filter, however, is typically formed from a moisture absorbent fiber mesh. During operation, as the filter receives particulate matter within the air sample, the filter also absorbs any moisture present within the air sample as well. The moisture changes the resonant frequency of the taut filter during operation, thereby affecting the accuracy of the resonant taut filter membrane sensing system in detecting the particulate mass concentration within an air sample.

Additionally, the material properties of the filter in the resonant taut filter membrane sensing system can affect the accuracy of the system's detection of the particulate mass concentration of an air sample. For the resonant taut filter membrane sensing system, the precision or accuracy of a particulate mass measurement depends upon the constancy of a radial tension of the filter membrane. However, as indicated, the filter is typically formed from a fiber mesh. Application of a radial tension to the fiber mesh, therefore, can cause weakening or tearing of the fiber mesh (e.g., mechanical instability within the filter) within certain areas of the membrane. The weakening of the filter in certain areas reduces the constancy of the radial tension within the filter (e.g., the uneven distribution of tension within the filter membrane). As such, a non-constant radial tension generated within the filter decreases the precision or accuracy of a particulate mass measurement made by the resonant taut filter membrane sensing system.

Also as described above, the conventional taut filter membrane sensing system is configured to oscillate the taut filter at higher, non-harmonic modes to allow for relatively sensitive measurement of particulate matter concentrations within an air sample. However, conventional filter membranes are formed from a fibrous material. During operation, therefore, the resonant taut filter membrane sensing system can generate a non-constant (i.e., inconsistent) radial tension within the filter. When the conventional taut filter membrane sensing system attempts to oscillate the taut filter at higher, non-harmonic modes, the non-constant radial tension within the filter limits the ability for the filter to vibrate at the desired non-harmonic modes. Such limited, upper mode vibration minimizes the accuracy of the membrane sensing system in detecting the particulate mass concentration within an air sample.

By contrast, embodiments of the present invention significantly overcome the described deficiencies and provide mechanisms and techniques for monitoring a mass concentration of particulate matter within a gas sample. A particulate mass monitor includes a controller that monitors a change in a resonant oscillation frequency of a taut metallic membrane, as caused by deposition of the particulate matter on the metallic membrane. The metallic membrane, such as a foil or metallized plastic film, is substantially mechanically stable under tension. Application of a tension to the periphery of the metallic membrane generates a substantially constant tension within the membrane, thereby allowing the particulate mass monitor to detect a particulate mass concentration of the air sample with a relatively high degree of accuracy. Additionally, the particulate mass monitor includes a membrane transporter that automatically advances the metallic membrane within the particulate mass monitor. The membrane transporter minimizes the necessity for manual replacement of the metallic membrane over time and allowing long term, unattended operation of the particulate mass monitor.

In one arrangement, a particulate mass monitor includes a metallic membrane, a particle collector directed at the metallic membrane, and a controller in electrical communication with the metallic membrane. The particle collector (e.g., electrostatic precipitator or impactor) is configured to direct particulate matter within an air sample to the metallic membrane. The controller is configured to generate and detect an oscillation frequency in the metallic membrane where the oscillation frequency of the metallic membrane is based upon the particulate matter collected by the metallic membrane. The metallic membrane is formed from a metallic material, such as a stainless steel material. As such, the metallic membrane is substantially mechanically stable under tension. When placed under tension, the metallic membrane maintains a substantially constant tension over time. Therefore, the use of the metallic membrane within the particulate mass monitor allows detection a particulate mass concentration of the air sample with a relatively high degree of accuracy, compared to a conventional taut filter membrane sensing system.

In one arrangement, the particulate mass monitor includes a membrane transporter coupled to the metallic membrane. The membrane transporter is configured to advance the metallic membrane relative to the particle collector such that a first metallic membrane portion orients in proximity to the particle collector during a first particulate mass monitor test and a second metallic membrane portion orients in proximity to the particle collector during a second particulate mass monitor test. The membrane transporter automatically advances the metallic membrane within the particulate mass monitor. The membrane transporter, therefore, minimizes the necessity for manual replacement of the metallic membrane over time and allows long term, unattended operation of the particulate mass monitor.

BRIEF DESCRIPTION OF THE DRAWINGS

The foregoing and other objects, features and advantages of embodiments of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 12A illustrates oscillation of the metallic membrane of FIG. 1 at a fundamental resonant oscillation frequency.

FIGS. 12B–12L illustrate oscillation of the metallic membrane of FIG. 1 at a higher modal oscillation frequency, the higher modal oscillation frequency based upon a fundamental resonant oscillation frequency of the metallic membrane.

DETAILED DESCRIPTION

Embodiments of the present invention provide mechanisms and techniques for monitoring a mass concentration of particulate matter within a gas sample. A particulate mass monitor includes a controller that monitors a change in a resonant oscillation frequency of a taut metallic membrane, as caused by deposition of the particulate matter on the metallic membrane. The metallic membrane, such as a foil or metallized plastic film, is substantially mechanically stable under tension. Application of a tension to the periphery of the metallic membrane generates a substantially constant tension within the membrane, thereby allowing the particulate mass monitor to detect a particulate mass concentration of the air sample with a relatively high degree of accuracy. Additionally, in one of the embodiments of the present invention, the particulate mass monitor includes a membrane transporter that automatically advances the metallic membrane within the particulate mass monitor. The membrane transporter minimizes the necessity for manual replacement of the metallic membrane over time and allowing long term, unattended operation of the particulate mass monitor.

Figure 1:
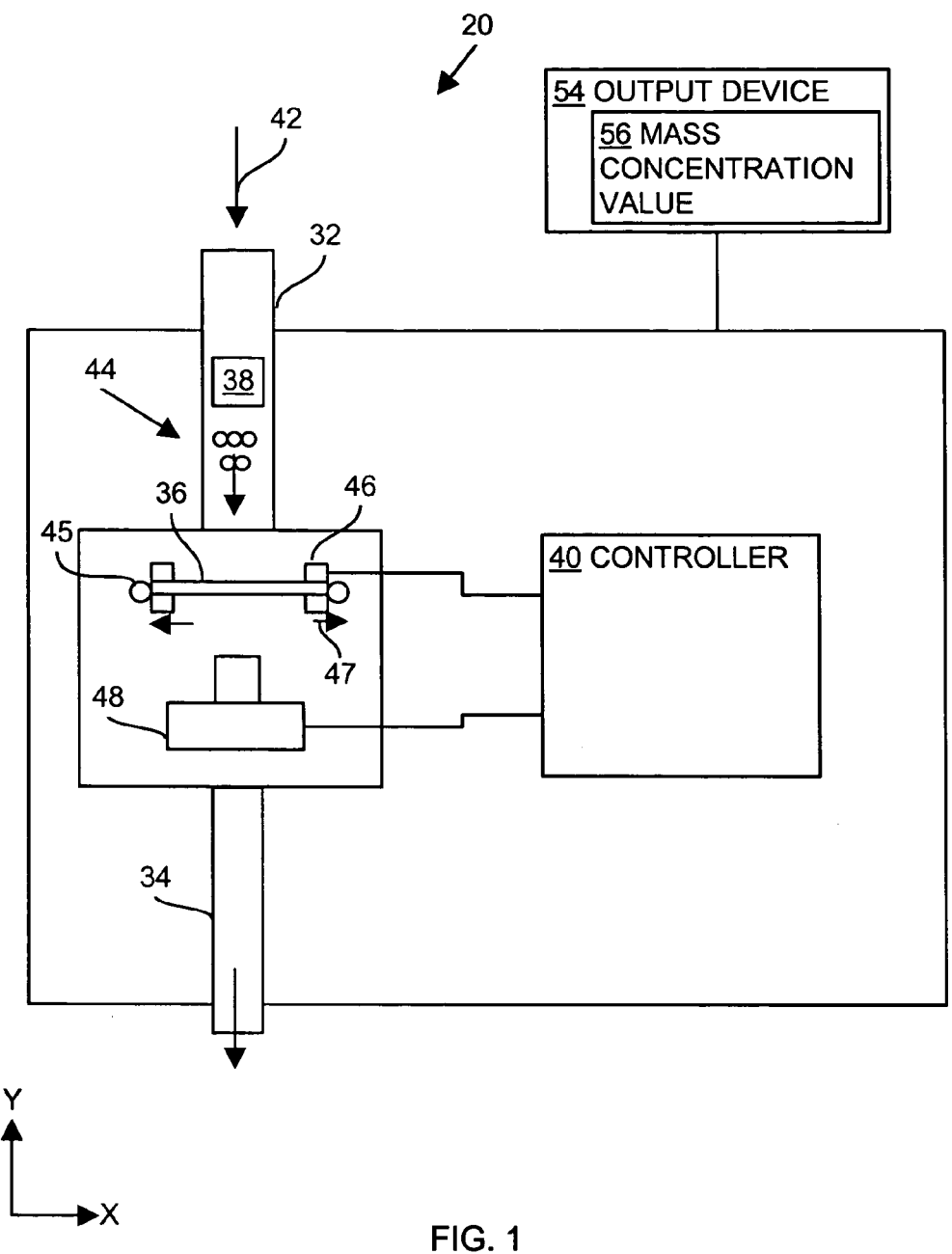
FIG. 1 illustrates a particulate mass monitor, according to one embodiment of the invention.

FIG. 1 shows an arrangement of a particulate mass monitor 20. The particulate mass monitor 20 is configured to monitor a fluid sample 42, such as a gas or air sample, from a fluid source for particulate matter (PM), such as within $PM_{10}$ (i.e., particulate matter having a size smaller than 10 micrometers), or $PM_{2.5}$ (i.e., particulate matter having a size smaller than 2.5 micrometers) particle size ranges. The particulate mass concentration of the air sample 42 relates to the particulate mass concentration of the fluid source. For example, as the particulate mass monitor 20 continuously receives the air sample 42 from an ambient air source, detection of a particulate mass concentration within the air sample 42 generally relates to the particulate mass concentration of the ambient air source. The particulate mass monitor 20 utilizes mechanical resonance mass sensing to monitor the particulate mass concentration of the air sample 42, as will be described below.

The particulate mass monitor 20 includes a fluid inlet 32 and a fluid outlet 34. The particulate mass monitor 20 also includes a taut metallic membrane 36, a particle collector 38, and a controller 40 in electrical communication with the metallic membrane 36.

The fluid inlet 32 is configured to direct an air sample or gas sample 42 toward the particle collector 38 of the particulate mass monitor 20. For example, in one arrangement, the fluid inlet 32 is configured with a geometry (e.g., as a nozzle or funnel) that directs a portion or sample 42 of ambient air, flowing relative to the particulate mass monitor 20, toward the particle collector 38. The fluid outlet 34 is configured to vent the air sample 42 from the particulate mass monitor 20 to the atmosphere.

The ambient air (e.g., the air sample 42) flows at a substantially constant flow rate through the particulate mass monitor 20. For example, the fluid inlet 32 or the fluid outlet 34 includes pump that draws an air sample 42 from the ambient air surrounding the particulate mass monitor 20 toward the particle collector 38. The pump maintains a substantially constant flow rate of fluid (e.g., a constant flow rate of the air sample 42) through the particulate mass monitor 20.

The metallic membrane 36 is formed from a metallic material, such as a stainless steel material or a metallized plastic material, such as Mylar plastic having a metal coating, for example. The metallic membrane 36 is configured as a substantially thin foil or film having a thickness of between approximately 0.0001 and 0.001 inches. The metallic membrane 36 orients relative to the particle collector 38 to receive particulate matter 44 within the air sample 42 carried by the fluid inlet 32. The metallic membrane 36 is configured to receive particulate matter 44 within the air sample 42.

In FIG. 1, the metallic membrane 36 is configured as a tensioned or taut metallic membrane 36 within the particulate mass monitor 20. Such tensioning results from application of a load or tension 47 to a periphery of the metallic membrane 36. As indicated above, for a mechanical resonance system, the precision or accuracy of a particulate mass measurement depends upon the constancy of tension of the sensing membrane (e.g., the metallic membrane 36). Because the metallic membrane 36 is formed from a metallic material, such as a stainless steel material or a metallized plastic material, the metallic membrane 36 is substantially mechanically stable under tension. Application of the load 47 to a periphery of the metallic membrane 36, therefore, generates a substantially constant tension within the metallic membrane 36 (e.g., a substantially even distribution of tension within the metallic membrane 36). Therefore, the use of the taut metallic membrane 36 within the particulate mass monitor 20 allows the particulate mass monitor 20 to detect a particulate mass concentration of the air sample with a relatively high degree of accuracy, such as compared to a conventional taut filter membrane sensing system.

In FIG. 1, the particle collector 38 orients in proximity to the metallic membrane 36 and is configured to direct particulate matter 44 within the air sample 42 toward the metallic membrane 36. The particle collector 38 aids in adhering the particulate matter 44 within the air sample 42 to the metallic membrane 36.

In one arrangement, the particle collector 38 is configured as an electrostatic precipitation device in combination with the metallic membrane 36. For example, in such an arrangement, the electrostatic precipitation device 38 is a sharp metallic point either at a positive or negative potential relative to the metal membrane 36 and creates a corona discharge that electrically charges the particulate matter 44 within the air sample 42 (i.e., the particulate matter 44 between the sharp point electrostatic precipitation device 38 and the metallic membrane 36). Based upon the potential difference between the electrostatic precipitation device 38 and the metallic membrane 36, the metallic membrane 36 electrostatically attracts the charged particulate matter 44 such that the charged particulate matter 44 travels from the electrostatic precipitation device 38 toward the metallic membrane 36 and adheres to the metallic membrane 36.

In one arrangement, the particulate mass monitor 20 having the electrostatic precipitation device 38 includes a pump. The pump creates a pressure differential between the particulate mass monitor 20 and the atmosphere to draw an air sample 42 from the surrounding ambient air into the particulate mass monitor 20. The fluid inlet 32 then directs the air sample 42 toward the electrostatic precipitation device 38 and past the corona discharge generated by the electrostatic precipitation device 38. Use of the pump and the fluid inlet 32 maximizes the particle collection efficiency of the particulate mass monitor 20 by forcing the air sample 42 through an ion stream (i.e., corona discharge) generated by the electrostatic precipitation device 38.

In one arrangement, the particulate mass monitor 20 having the electrostatic precipitation device 38 does not utilize a pump. In order to direct an air sample 42 into the particulate mass monitor 20 and past the electrostatic precipitation device 38, the electrostatic precipitation device 38, when ionizing the air molecules, is configured to create an ion wind effect. The ion wind effect causes the air sample 42 to flow relative to (i.e., into) the particulate mass monitor 20, thereby providing the particulate mass monitor 20 with a substantially continuously flowing air sample 42 during operation.

For example, assume the particulate mass monitor 20 is configured such that the fluid inlet 32 is open to the ambient air (i.e., without any pre-collection stage). As the electrostatic precipitation device 38 produces a corona discharge, the corona discharge creates an air flow directed from the electrostatic precipitation device 38 towards the metallic membrane 36, as caused by an ion wind effect. The ion wind results from collisions between the ions generated in the gas (e.g., air) traveling from the electrostatic precipitation device 38 and the air molecules in the vicinity of the electrostatic precipitation device 38. The ion wind induces an air or gas flow rate within the particulate mass monitor 20 of approximately 10 liters/minute or more at a corona current of approximately of 5 µA (the flow rate being proportional to the square root of the corona current). As such, the ion wind generated by the electrostatic precipitation device 38 during operation draws the air sample 42 into the particulate mass monitor 20 in a substantially continuous manner.

With the electrostatic precipitation device 38 configured to create an ion wind effect relative to the particulate mass monitor 20, the electrostatic precipitation device 38 allows the particulate mass monitor 20 to operate without the use of a pump or mechanically dynamic components. As such, the electrostatic precipitation device 38 allows substantially silent operation particulate mass monitor 20, such as applicable to indoor air quality measurements where pump noise is typically unacceptable.

In another arrangement, the particle collector 38 is configured as a jet impactor. For example, in such an arrangement, the particle collector 38 is configured either as a single nozzle or a multiplicity of nozzles to increase a velocity of the air sample 40 flowing through the particulate mass monitor 20. The particle collector 38 nozzle (or nozzles) directs both the air sample 40 and the particulate matter 44 within the air sample 42 toward the metallic membrane 36 at a relatively high velocity, thereby causing the particles 44 to impact onto the metallic membrane 36. An adhesive coating on the surface of the metallic membrane 36 can be used to ensure the retention of the particles collected on the metallic membrane 36.

Another variation using jet impaction to collect the particulate matter on the metallic membrane 36 includes a series of consecutive impaction stages wherein the nozzle (or nozzles) at each consecutive impaction stage have decreasing openings (i.e. decreasing opening diameters) resulting in correspondingly increasing air velocities. This configuration, called a cascade impactor separates particulate matter by size. The combination of this impaction configuration with mass sensing of the taut metal membrane resonance provides a measurement of the particle size distribution of the sampled particulate matter.

The controller 40 is configured to detect a mass concentration of particulate matter 44 within the air sample 42 based upon a mechanical resonance or oscillation of the metallic membrane 36. For example, the controller 40 electrically couples with the metallic membrane 36 and is configured to generate an oscillation frequency in the metallic membrane 36. The controller 40 oscillates or induces a vibration in the metallic membrane 36 where the resonant oscillation of the metallic membrane 36 is based upon the overall mass of the metallic membrane 36 (i.e., the mass of the metallic membrane 36 and any particulate matter 44 collected by the metallic membrane 36 over time). Furthermore the controller 40 is configured to detect or monitor the resonant oscillation frequency of the metallic membrane 36 over time. Changes in the resonant oscillation frequency of the metallic membrane 36, as detected by the controller 40 and caused by deposition of the particulate matter 44 on the metallic membrane 36, relate to a particulate mass concentration of the air sample 42.

The controller 40, in one arrangement, includes an output device 54 configured to provide, to a user, a particulate mass concentration value 56 associated with the particulate mass concentration of the air sample 42. The particulate mass concentration value 56 indicates, to the user, a level or indicator as to ambient air quality. In one arrangement, the output device 54 is configured as a display, such as a liquid crystal display or a light emitting diode display, to provide the particulate mass concentration value 56 to a user. In another arrangement, the output device 54 is configured as a digital data output port to provide the particulate mass concentration value 56 to a user.

In one arrangement, the controller 40 includes an oscillation element 46 coupled to the metallic membrane 46 and electrically coupled to the controller 40. The oscillation element 46 is configured to generate the oscillation frequency in the metallic membrane 36. The oscillation element 46, in one arrangement, induces an oscillation frequency, such as a resonance frequency, in the metallic membrane 36 using a piezoelectric element. In another arrangement, the oscillation element 46 induces an oscillation frequency, such as a resonance frequency, in the metallic membrane 36 using an oscillatory electric or magnetic field.

In one arrangement, the controller 40 includes a detector element 48 oriented in proximity to the metallic membrane 36 and electrically coupled to the controller 40. The detector element 48 is configured to detect the resonant oscillation frequency of the metallic membrane 36, as induced by the controller 40. The detector element 48, in various arrangements, is configured as an optical, acoustic, or electric detector, to detect the oscillation frequency of the metallic membrane 36 during operation.

Figure 2:
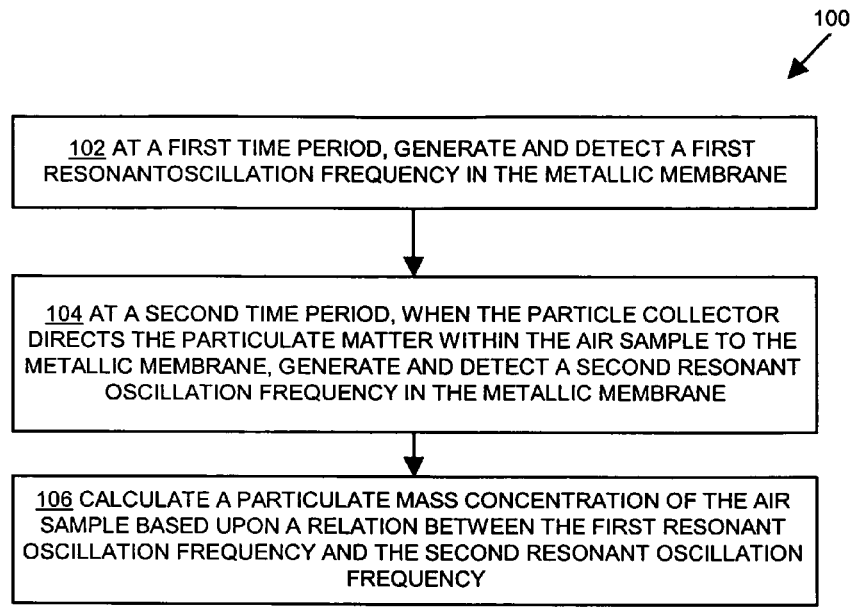
FIG. 2 illustrates a flow chart of a procedure performed by the particulate mass monitor of FIG. 1, according to one embodiment of the invention.
Figure 3:
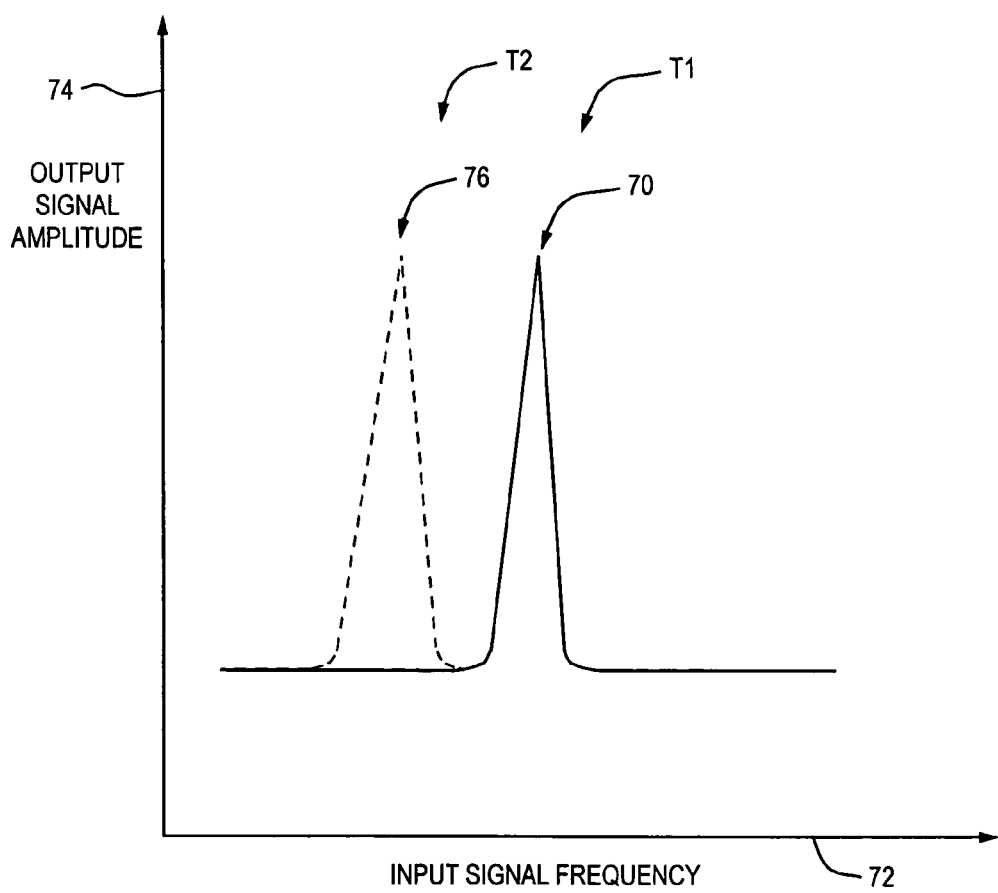
FIG. 3 illustrates a change in resonant frequency of a metallic membrane, used in the particulate mass monitor of FIG. 1, during operation of the particulate mass monitor, according to one embodiment of the invention.

FIG. 2 is a flow chart 100 of a procedure performed by the particulate mass monitor 20. FIG. 3, taken with FIGS. 1 and 3, illustrates a graph representing resonant oscillation frequencies induced in the metallic membrane 36 by the controller 40 during operation. The controller 40 monitors a change in the resonant oscillation frequency of the metallic membrane 36, as caused by deposition of the particulate matter 44 on the metallic membrane 36. Based upon the change in the resonant oscillation frequency of the metallic membrane 36, the controller 40 detects a mass concentration of particulate matter 44 within the air sample 42, the mass concentration indicative of ambient air quality.

In step 102, at a first time period T1, the controller 40 generates and detects a first resonant oscillation frequency 70 in the metallic membrane 46. The first resonant oscillation frequency 70 of the metallic membrane 36 provides the controller 40 with a baseline resonant oscillation measurement related to the metallic membrane 36. As the metallic membrane 36 collects particulate matter within the air sample 42 over time, the controller 40 uses the baseline resonant oscillation measurement as a reference to measure changes in the resonant oscillation frequency of the metallic membrane 36 caused by collection of the particulate matter 44 by the metallic membrane 36.

In one arrangement, the controller 40 is configured to induce the first resonant oscillation frequency 70 in the metallic membrane 36. The resonant frequency is defined as the natural oscillation of a mechanical system (e.g., the metallic membrane 36) proportional to the square root of the ratio of the system stiffness constant (e.g., a metallic membrane stiffness constant) and the system mass (e.g., a metallic membrane mass). In such an arrangement, the controller 40, the oscillation element 46, and the detector element 48 form a mechanical resonance feedback loop system to iteratively detect and generate the resonant frequency in the metallic membrane 36.

For example, referring to FIG. 3, the controller 40 transmits an input signal 72, such as a sine wave having a particular frequency, to the oscillation element 46, thereby causing the oscillation element 46 to oscillate the metallic membrane 36 at or near the resonant frequency of the metallic membrane 36. In a substantially simultaneous manner, the controller 40 retrieves an output signal 74 from the detector element 48 where the output signal 74 indicates the vibration or oscillation of the metallic membrane 36 in response to the input signal 70. The controller 40 then iteratively adjusts the frequency of the input signal 72, based upon the output signal 74 from the detector element 48 (i.e., using the mechanical resonance feedback loop system). When the controller 40 detects, based upon the output frequency 74 measured by the detector element 48, that a given input signal frequency produces a maximal vibration or oscillation of the metallic membrane 36, such as the first resonant oscillation frequency 70, the controller 40 maintains the oscillation (i.e., the first oscillation frequency) in the membrane 36. Such maximal vibration or oscillation of the metallic membrane 36 represents the resonant frequency of the metallic membrane 36.

Returning to FIG. 2, in step 104, at a second time period T2, when the particle collector 38 directs the particulate matter 44 within the air sample 42 to the metallic membrane 32, the controller 40 generates and detects a second resonant oscillation frequency 76 in the metallic membrane 36. For example, as the particle collector 38 deposits particulate matter 44 onto the metallic membrane 36 during operation, the mass of the metallic membrane 36 increases (i.e., as a combination of the mass of the metallic membrane 36 and the mass of the particles 44). As the mass of the metallic membrane 36 increases, the resonant frequency of the metallic membrane 36 decreases. To generate the resonant frequency of the metallic membrane 36 having the additional particulate matter, the controller 40 decreases (i.e., by sweeping) the frequency of the input signal 72.

For example, as the resonant frequency of the metallic membrane 36 changes after receiving the particulate matter within the air sample 42, the controller 40 iteratively decreases the input frequency 72 to the membrane 36, via the oscillation element 46 and detects the output signal 74, via the detector element 48. When the controller 40 detects that the decreased input signal frequency 72 produces a shifted maximal vibration or oscillation of the metallic membrane 36, such as the second resonant oscillation frequency 76, the controller 40 maintains the oscillation (i.e., the second resonant oscillation frequency 76) in the membrane 36.

In step 106, the controller 40 calculates a particulate mass concentration of the air sample 42 based upon a relation between the first resonant oscillation frequency 70 and the second resonant oscillation frequency 76. For example, assume the controller 40 stores, such as in a memory location, the first resonant oscillation frequency 70 and the second resonant oscillation frequency 76. Using the following relationship:

$$\Delta m = m_0[(f_0/f_f)^2 - 1]$$

where $m_0$ is the total initial mass of the resonating system, $f_0$ is the first resonant oscillation or resonance frequency 70 of the metallic membrane 36 (e.g., before particle collection), and $f_f$ is the second resonant oscillation frequency 76 of the metallic membrane 36, the controller 40 calculates $\Delta m$ where $\Delta m$ is the mass increment of collected particulate matter that represents the particulate mass concentration of the air sample 42. After calculating the particulate mass concentration, the controller 40 provides the result as a particulate mass concentration value 56 using the output device 54, thereby providing, to a user, an indicator as to ambient air quality.

As indicated above, the metallic membrane 36 is configured as a tensioned or taut metallic membrane 36 within the particulate mass monitor 20. For a mechanical resonance system, the precision or accuracy of a particulate mass measurement, and therefore, accurate detection of a particulate mass concentration of the air sample 42, depends upon the constancy of tension of the metallic membrane 36. Because the metallic membrane 36 is formed from a substantially uniform metallic material (i.e., having substantially uniform material properties), such as a stainless steel material or a metallized plastic material, the metallic membrane 36 is substantially mechanically stable under tension. Application of the load 47 to a periphery of the metallic membrane 36, therefore, generates a substantially constant tension within the metallic membrane 36 (i.e., a substantially even distribution of tension within the metallic membrane 36). Therefore, the use of the taut metallic membrane 36 within the particulate mass monitor 20 allows the particulate mass monitor 20 to detect a particulate mass concentration of the air sample with a relatively high degree of accuracy (e.g., such as compared to a conventional taut filter membrane sensing system).

Figures 4, 5:
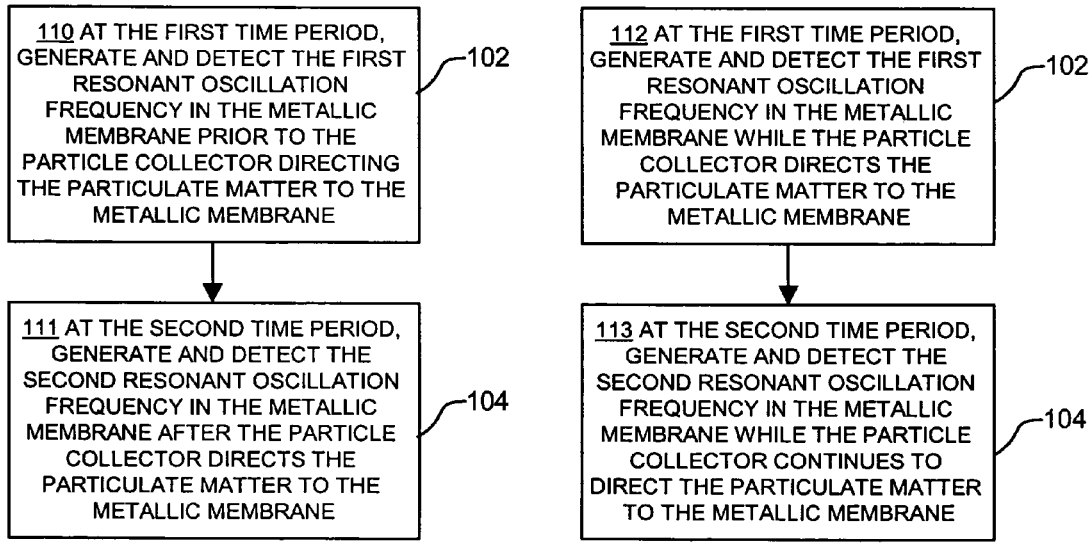
FIG. 4 illustrates a flow chart of a procedure performed by the particulate mass monitor of FIG. 1, according to one embodiment of the invention.
FIG. 5 illustrates a flow chart of a procedure performed by the particulate mass monitor of FIG. 1, according to one embodiment of the invention.

FIG. 4 illustrates, in one arrangement, steps performed by the controller 40 as the controller 40 detects a mass concentration of particulate matter 44 within the air sample 42. For example, FIG. 4 illustrates the controller 40 detecting the first and second resonant oscillation frequencies of the metallic membrane 36 when providing particulate matter 44 to the metallic membrane 36 in an interrupted manner.

In step 110, at the first time period, the controller 40 generates and detects the first resonant oscillation frequency in the metallic membrane 36 prior to the particle collector 38 directing the particulate matter 44 to the metallic membrane 36. The controller 40, as such, measures the resonant oscillation of the metallic membrane 36 before the metallic membrane collects particulate matter 44 from the air sample 42. For example, as indicated above, when the particle collector 38 is configured as an electrostatic precipitation device 38, the electrostatic precipitation device 38 creates an ion wind effect when ionizing the gas molecules within an air sample 42. The ion wind results from collisions between the ions (i.e., ionized gas molecules) traveling from the electrostatic precipitation device 38 and the air molecules in the vicinity of the electrostatic precipitation device 38. As the ionic wind effect causes the air sample 42 to flow within the particulate mass monitor 20, the air sample 42 impacts the metallic membrane 36. Such impaction between the air sample and the metallic membrane 36 affects the resonant oscillation frequency of the metallic membrane 36.

In the case where the metallic membrane 36 oscillates at the resonant frequency, contact between the air sample 42 and the metallic membrane 36 causes the metallic membrane 36 to oscillate at a shifted resonant frequency, thereby affecting the accuracy of a particulate mass measurement made by the particulate mass monitor 20. By generating and detecting the first resonant oscillation frequency in the metallic membrane 36 prior to the particle collector 38 directing the particulate matter 44 to the metallic membrane 36, the controller 40 allows the metallic membrane 36 to oscillate at the resonant frequency, without influence of the ionic wind effect on the oscillation of the membrane 36. As such, the controller 40 provides a relatively high level of accuracy to the particulate mass measurement made by the particulate mass monitor 20.

In step 111, at the second time period, the controller 40 generates and detects the second oscillation frequency in the metallic membrane 36 after the particle collector 38 directs the particulate matter 38 to the metallic membrane 36. Similar to step 110, to minimize the effect of the ion wind on the resonant frequency oscillation of the metallic membrane 36, the controller 40 measures the second resonant oscillation frequency in the metallic membrane 36 once the particle collector 38 has completed generation of the electrostatic discharge to transmit the particulate matter 44 to the metallic membrane 36. Therefore, as the controller 40 detects the second resonant oscillation frequency in the metallic membrane 36, the controller performs such detection in the absence of an ionic wind. By generating and detecting the second resonant oscillation frequency in the metallic membrane 36 after the particle collector 38 completes the step of directing the particulate matter 44 to the metallic membrane 36, the controller 40 allows the metallic membrane 36 to oscillate at the resonant frequency, without influence of the ionic wind effect on the resonant oscillation of the membrane 36. As such, the controller 40 provides a relatively high level of accuracy to the particulate mass measurement made by the particulate mass monitor 20.

FIG. 5 illustrates, in one arrangement, steps performed by the controller 40 as the controller 40 detects a mass concentration of particulate matter 44 within the air sample 42. For example, FIG. 5 illustrates the controller 40 detecting the first and second resonant oscillation frequencies of the metallic membrane 36 when providing particulate matter 44 to the metallic membrane 36 in a substantially uninterrupted manner.

In step 112, at the first time period, the controller 40 generates and detects the first resonant oscillation frequency in the metallic membrane 36 while the particle collector 38 directs the particulate matter 44 to the metallic membrane 36. The controller 40, as such, measures the first resonant oscillation frequency of the metallic membrane 36 while the metallic membrane 36 collects particulate matter 44 from the air sample 42.

In step 113, at the second time period, the controller 40 generates and detects the second resonant oscillation frequency in the metallic membrane 36 while the particle collector continues to direct the particulate matter to the metallic membrane. The controller 40, as such, measures the second resonant oscillation frequency of the metallic membrane 36 while the metallic membrane 36 continuously collects particulate matter 44 from the air sample 42. By detecting the first and second resonant oscillation frequencies of the metallic membrane 36 as the metallic membrane 36 collects particulate matter, the controller 40 allows substantially continuous operation of the particulate mass monitor 20.

Figure 6:
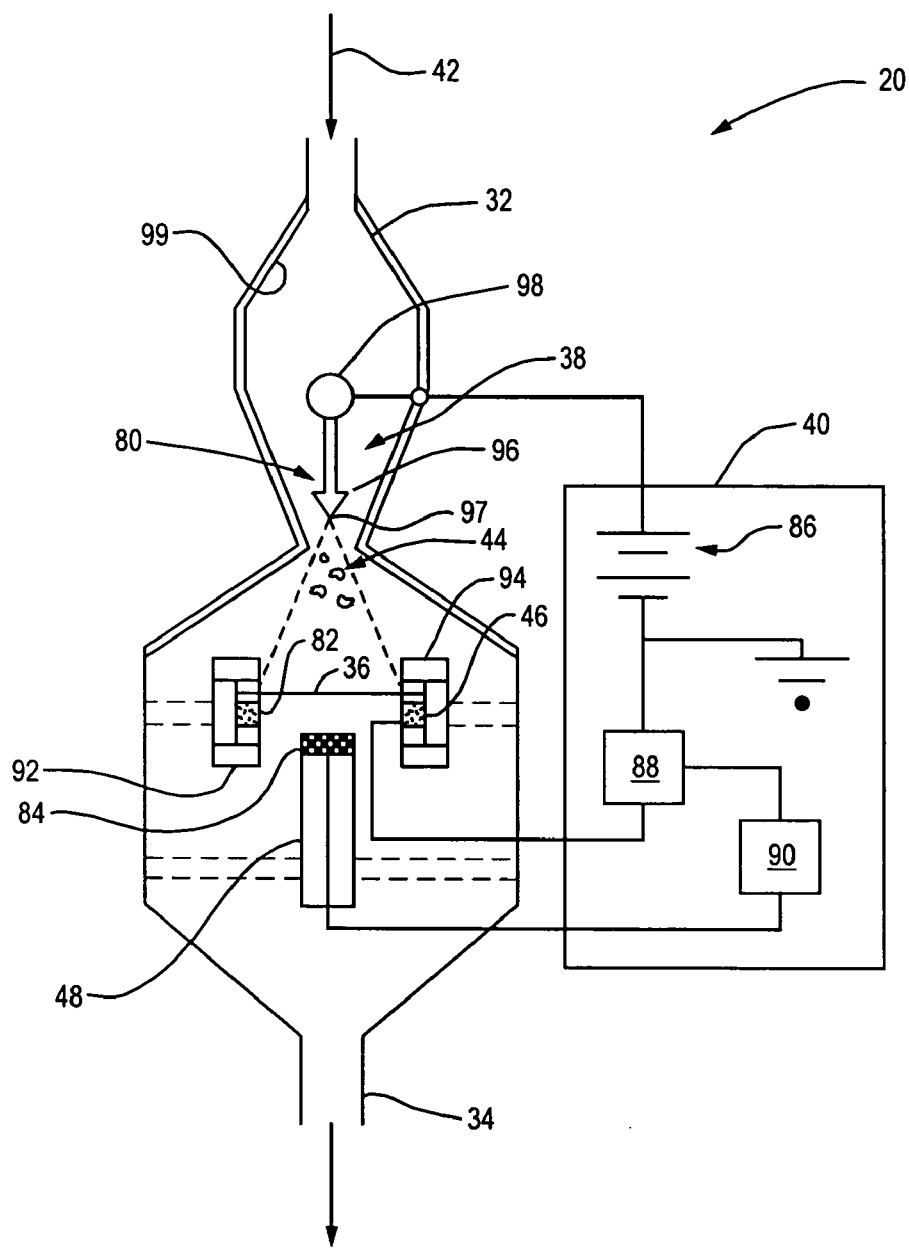
FIG. 6 illustrates an arrangement of a particulate mass monitor of FIG. 1, according to one embodiment of the invention.
Figure 7:
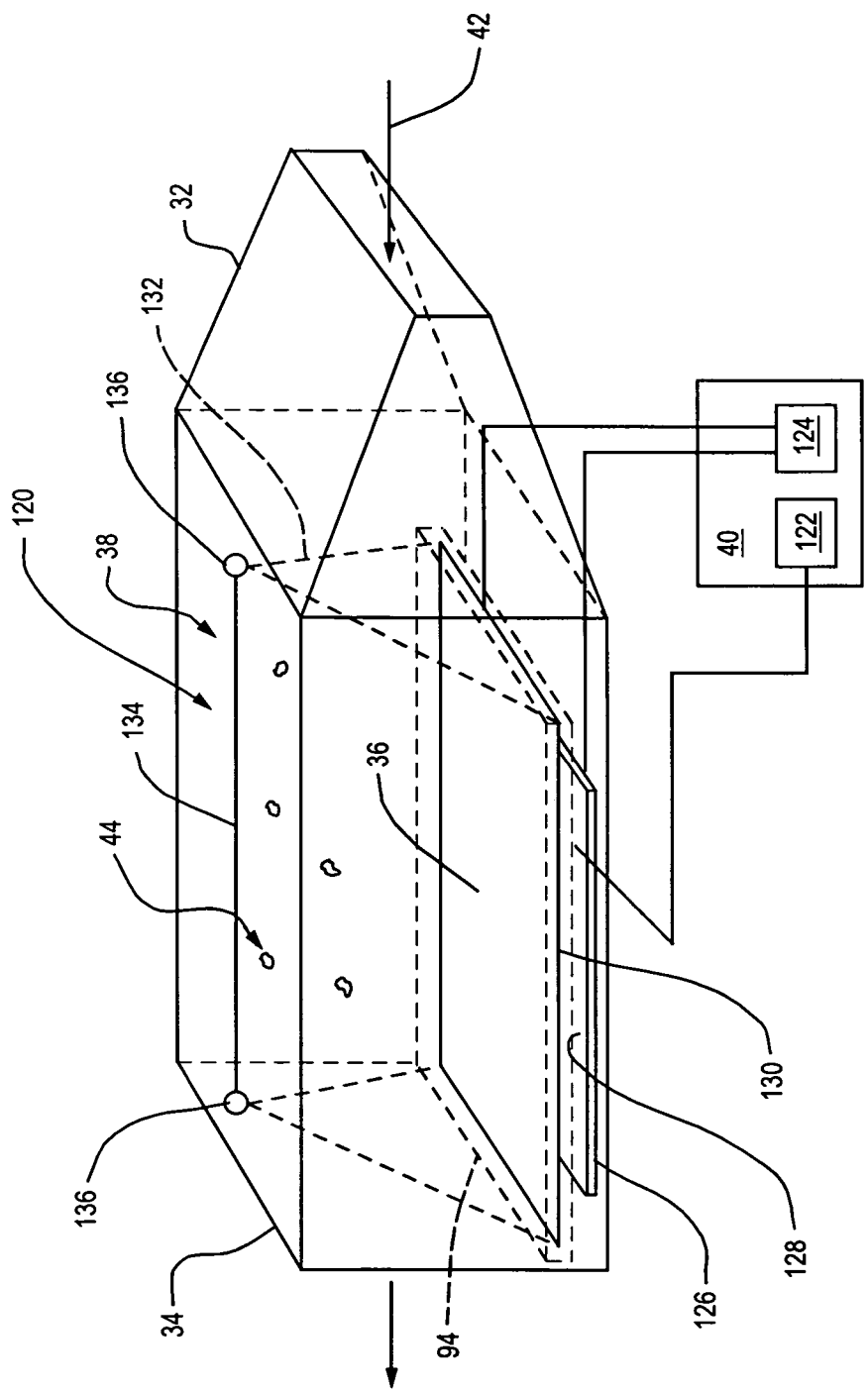
FIG. 7 illustrates an arrangement of a particulate mass monitor of FIG. 1, according to one embodiment of the invention.

Returning to FIG. 1, as indicated above, the particle collector 38, in one arrangement, is configured as an electrostatic precipitation device. Also as indicated above, the oscillation element 46 induces an oscillation or resonance frequency in the metallic membrane 36 using a piezoelectric element or using an oscillatory electric or magnetic field. Additionally the detector element 48 is configured as an acoustic or electric detector, to detect the resonant oscillation frequency of the metallic membrane 36 during operation. FIGS. 6 and 7 illustrate example arrangements of the particulate mass monitor 20 having combinations of the described configurations of the particle collector 38, the oscillation element 46, and the detector element 48.

FIG. 6 illustrates an arrangement of the particulate mass monitor 20 where the particle collector 38 is configured as a point-to-plane electrostatic precipitation device 80, the oscillation element 46 is configured as a mechanical oscillator such as a piezoelectric driver 82, and the detector element 48 is configured as a microphone 84. The controller 40 includes a constant current, high-voltage power supply 86 coupled to the point-to-plane electrostatic precipitation device 80, a sine wave synthesizer 88 coupled to the piezoelectric driver 82, and a resonance sensing circuit 90 coupled to the microphone 84. A user utilizes the particulate mass monitor 20 configured with the point-to-plane electrostatic precipitation device 80 for ambient air monitoring or for indoor air quality measurements, for example.

The piezoelectric driver 82, such as a ring-shaped piezo crystal, mounts in direct mechanical contact with the taut metallic membrane 36. For example, in one arrangement, the piezoelectric driver 82 forms part of a membrane frame 92 having a membrane tensioning mechanism 94. The piezoelectric driver 82 is configured to receive an input frequency (i.e., variable frequency) from the sine wave synthesizer 88. The piezoelectric driver 82 vibrates or oscillates based upon the input frequency from the sine wave synthesizer 88 and transmits the oscillation to the metallic membrane 36.

The microphone 84 is configured as an acoustic detector to detect the oscillation of the metallic membrane 36 based upon the sine wave input frequency provided by the sine wave synthesizer 88. The microphone 84, in one arrangement, orients in proximity to the metallic membrane 36 in a location downstream to a direction of the flow of the air sample 42. During operation, as the piezoelectric driver 82 oscillates the metallic membrane 36, the microphone 84 receives an acoustic signal generated by the oscillating membrane 36 and transmits a corresponding output signal to the resonance sensing circuit 90. The resonance sensing circuit 90 (i.e., a processor of the controller 40) utilizes the output signal to adjust the input frequency provided from the sine wave synthesizer 88 to the piezoelectric driver 82. When the resonance sensing circuit 90 detects, based upon the output signal provided by the microphone 84, that a given input frequency produces a maximal vibration or oscillation of the metallic membrane 36, the resonance sensing circuit 90 directs the sine wave synthesizer 88 to maintain the input frequency to the membrane 36 to maintain maximal vibration or oscillation.

The point-to-plane electrostatic precipitation device 80 is configured to generate and deliver a corona discharge relative to the metallic membrane 36 (i.e., a conically shaped corona discharge). The geometry of the point-to-plane electrostatic precipitation device 80 is configured to minimize or limit the presence of sharp edges in order to prevent generation of corona discharges at unwanted locations of the electrostatic precipitation device 80. For example, the point-to-plane electrostatic precipitation device 80 includes a point electrode 96 and a delivery element 98. The point electrode 96 defines either a positive or negative electrical potential relative to the metal membrane 36 and is configured with a corona discharge point 97 facing the metallic membrane 36. The point-to-plane electrostatic precipitation device 80 also includes a delivery element 98 that delivers current at a high positive or negative voltage from the power supply 86 to the point electrode 96. The delivery element 98 is configured as having a sphere shape (e.g., an anti-corona sphere) to minimize or limit the presence of sharp edges of the electrostatic precipitation device 80. The delivery element 98 couples to the constant current, high voltage power supply 86 of the controller 40. The power supply 86 maintains a substantially constant corona current for the electrostatic precipitation device 80, thereby minimizing the effect of changes in operating parameters, such as air density, humidity, surface condition of the corona point, on the generation of the corona discharge.

During operation, the delivery element 98 delivers the substantially constant current to the point electrode 96. The point electrode 96 receives the current, and the corona discharge point 97 of the point electrode 96 ionizes the air or gas molecules within the air sample 42 in the vicinity of the point electrode 96 which ions, in turn impart an electric charge to the particulate matter 44 within the air sample 42. With the point electrode 96 forming either a positive or negative potential relative to the metal membrane 36, the metal membrane 36 electrostatically attracts the oppositely charged particulate matter 44.

In one arrangement, in the case where the particulate mass monitor 20 includes the point-to-plane electrostatic precipitation device 80, the fluid inlet 32 includes an electrically conductive inner surface 99 having an electrical potential equal to the electrical potential of the point electrode 96. Such a configuration minimizes collection of electrically charged particulate matter 44 by the inner surface 99 of the fluid inlet and maximizes the amount of particulate mater 44 directed toward the metallic membrane 36 during operation.

FIG. 7 illustrates an arrangement of the particulate mass monitor 20 where the particle collector 38 is configured as a wire-to-plane electrostatic precipitation device 120, the oscillation element 46 is configured as an electrical oscillator such as a capacitive driver 122, and the detector element 48 is configured as an electrical detector, such as a capacitive charge detector 124. In one arrangement, the controller 40 operates the capacitive driver 122 and the capacitive charge detector 124. A user utilizes the particulate mass monitor 20 configured with the wire-to-plane electrostatic precipitation device 120 for continuous source emission monitoring. For example, the user orients the particulate mass monitor 20 relative to a flow direction of the air sample 42 such that the air sample 42 flows though the particulate mass monitor 20 without the use of a pump associated with the particulate mass monitor 20 (e.g., such as in stack gas monitoring).

Because the oscillating element within the particulate mass monitor 20 is configured as a taut metallic membrane 36 (e.g., where the tensioning mechanism 94 applies a tension to the metallic membrane 36 about a periphery of the membrane 36), the metallic membrane 36 functions as one of two electrodes of a parallel plate capacitor. The particulate mass monitor 20, therefore, includes a conductive plate 126 defining a substantially planar surface 128. The conductive plate 126 orients in proximity, and substantially parallel, to a substantially planar surface 130 defined by the metallic membrane 36.

The capacitive driver 122 electrically couples with the metallic membrane 36 and the conductive plate 126. The capacitive driver 122, in one arrangement, is configured as an electronic circuit, such as a variable frequency sine wave oscillator, configured to apply an alternating electrical potential between the metallic membrane 36 and the conductive plate 126. When applying the alternating potential between the metallic membrane 36 and the conductive plate 12, the capacitive driver 122 creates a corresponding, periodic deflection in the metallic membrane 36. During operation, the capacitive driver 122 imposes a drive frequency to the metallic membrane 36 where the drive frequency is one-half the oscillation frequency of the metallic membrane 36. For example, if the capacitive driver 122 provides a drive frequency of 5,000 Hz to the metallic membrane 36, the metallic membrane 36 oscillates at a frequency of 10,000 Hz because for every cycle of the drive signal, the metallic membrane 36 deflects twice from a rest position.

The capacitive charge detector 124 electrically couples with either the conductive plate 126, or the metallic membrane 36, or both the conductive plate 126 and the metallic membrane 36. The capacitive charge detector 124, in one arrangement is configured as an electronic circuit that measures the varying capacitance that results from the oscillation or time-varying deflection of the metallic membrane 36. Based upon the varying capacitance between the conductive plate 126 and the metallic membrane 36, the capacitive charge detector 124 detects the resonant oscillation frequency in the metallic membrane 36.

The wire-to-plane electrostatic precipitation device 120 is configured to generate and deliver a corona discharge relative to the metallic membrane 36 (i.e., a triangular or "tent-shaped" corona discharge). The geometry of the wire-to-plane electrostatic precipitation device 120 is configured to minimize the presence of sharp edges of the precipitation device 120 in order to prevent corona discharges at unwanted locations of the electrostatic precipitation device 80. The wire-to-plane electrostatic precipitation device 120 includes a wire electrode 134 and current delivery elements 136. The wire electrode 134 defines either a positive or negative electrical potential relative to the metallic membrane 36 (e.g., a rectangularly-shaped metallic membrane 36). The delivery elements 136 are configured as having a sphere shape (e.g., an anti-corona sphere) to minimize or limit the presence of sharp edges of the electrostatic precipitation device 80. The delivery element 98 couples to a constant current, high voltage power supply, such as associated with the controller 40. The power supply 86 maintains a substantially constant corona current for the electrostatic precipitation device 120, thereby minimizing the effect of changes in operating parameters, such as air density, humidity, surface condition of the corona point, on the generation of the corona discharge.

During operation, the delivery elements 136 provide the substantially constant corona current to the wire electrode 134. The wire electrode 134 produces, in turn, a corona discharge to charge or ionize the particulate matter 44 within the air sample 42 in the vicinity of the wire electrode 134. With the wire electrode 134 forming either a positive or negative potential relative to the metal membrane 36, the metal membrane 36 electrostatically attracts the oppositely charged particulate matter 44.

FIGS. 1, 6, and 7 illustrate configurations of the particulate mass monitor 20 having a single metallic membrane 36 that forms part of a single sensing stage. However, during operation, variations in temperature of the air sample 42 over time can affect the resonant oscillation frequency of the metallic membrane 36. In turn, such an effect on the resonant oscillation frequency of the metallic membrane 36 reduces the accuracy of the measurement of the particulate mass concentration of an air sample 42.

Figure 8:
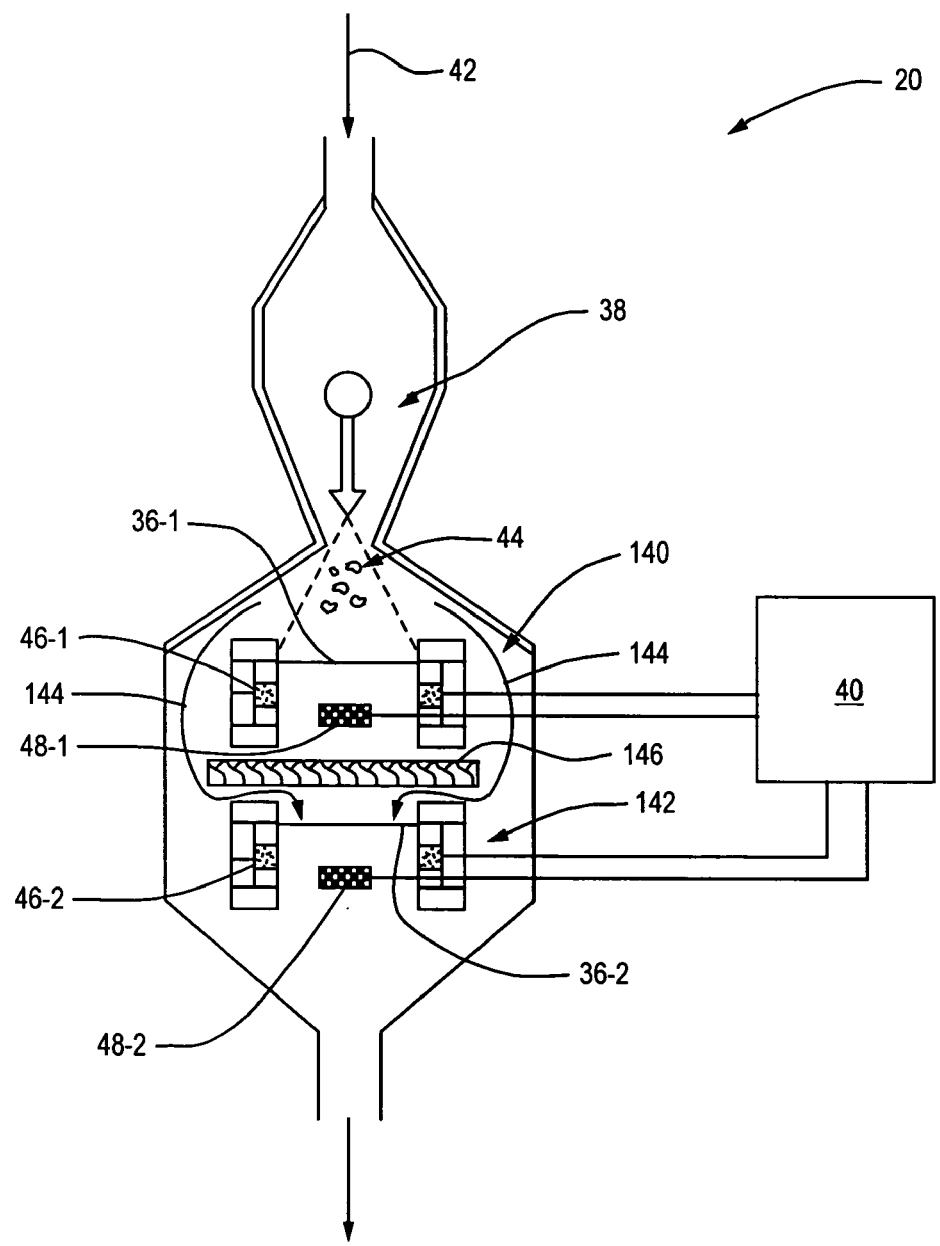
FIG. 8 illustrates an arrangement of a particulate mass monitor of FIG. 1 having a first stage sensor and a second stage sensor, according to one embodiment of the invention.

FIG. 8 illustrates an arrangement of the particulate mass monitor 20 where the particulate mass monitor 20 includes two sensing stages 140, 142. The particulate mass monitor 20 has a first sensing stage 140 having a first metallic membrane 36-1 and a second sensing stage 142 having a second metallic membrane 36-2. In such an arrangement, the particulate mass monitor 20 substantially isolates the second metallic membrane 36-2 from the particulate matter delivered to the first metallic membrane 36-1 by the particle collector 38. For example, in one arrangement, the particulate mass monitor 20 includes the first sensing stage 140 and the second sensing stage 142 arranged in series and separated by a barrier 146. The barrier 146 provides physical and acoustic isolation of the first sensing stage 140 from the second sensing stage 142. In one arrangement, the barrier 146 is configured as a particle filter to minimize or eliminate the presence of particulate matter within the air sample 144.

During operation, the controller 40 compares the resonant oscillation frequencies of the first metallic membrane 36-1 and the second metallic membrane 36-2 both before and after the particle collector 38 directs the particulate matter 44 to the first metallic membrane 36-1. Such comparison minimizes or eliminates the effect that a variance in the temperature of the air sample 42 has on the air sample mass concentration measurements made by the particulate mass monitor 20 over time. As such the use of the two sensing stages 140, 142 increases the accuracy of the air sample mass concentration measurements made by the particulate mass monitor 20. The following outlines the theory behind the use of two sensing stages.

If the metallic membranes 36-1, 36-2 have similar masses and tensions, their respective resonance frequencies will also be similar (although the resonance frequencies of the metallic membranes 36-1, 36-2 are unlikely to be identical). As indicated above, the basic mass sensing equation for a resonating metallic membrane, is given as:

$$\Delta m = m_0[(f_0/f_f)^2 - 1] \quad (1)$$

where $\Delta m$ is the mass increment, $f_0$ is the initial or tare resonant frequency, $f_f$ is the resonant frequency after particle collection, and $m_0$ is the initial or tare mass of the metallic membrane.

For a two-stage system, an initial ratio of resonant frequencies $R_0$ is given as:

$$R_0 = f_{0m}/f_{0r} \quad (2)$$

where $f_{0m}$ is the initial or tare frequency of the first or mass sensing stage 140 and $f_{0r}$ is the initial frequency of the second or reference stage 142. After sampling, or during the run, a new ratio $R_f$ is defined by:

$$R_f = f_{fm}/f_{fr} \quad (3)$$

where $f_{fm}$ and $f_{fr}$ are the resonant frequencies of the metallic membranes 36-1, 36-2 of the mass sensing stage 140 and the reference stage 142, respectively, after particle collection has occurred on the first metallic membranes 36-1 in the first stage 140. Equation (1), therefore, becomes:

$$\Delta m = m_0[(R_0/R_f)^2 - 1] \quad (4)$$

where $R_0$ is the reference ratio of the resonant frequencies, (e.g., as stored in memory associated with the controller 40 during a run and updated at the start of every run). The value $R_f$ decreases as particle collection by the first metallic membranes 36-1 occurs. Equation (4), therefore, is based upon the relative resonant oscillation frequencies of the first 36-1 and second 36-2 metallic membranes. Any drifting or change in the resonant frequencies of the first metallic membrane 36-1 and the second metallic membrane 36-2 as caused by changes in temperature, air density, or gravity, for example, are minimized or eliminated because the changes affects equally both $R_0$ and $R_f$.

Figure 9:
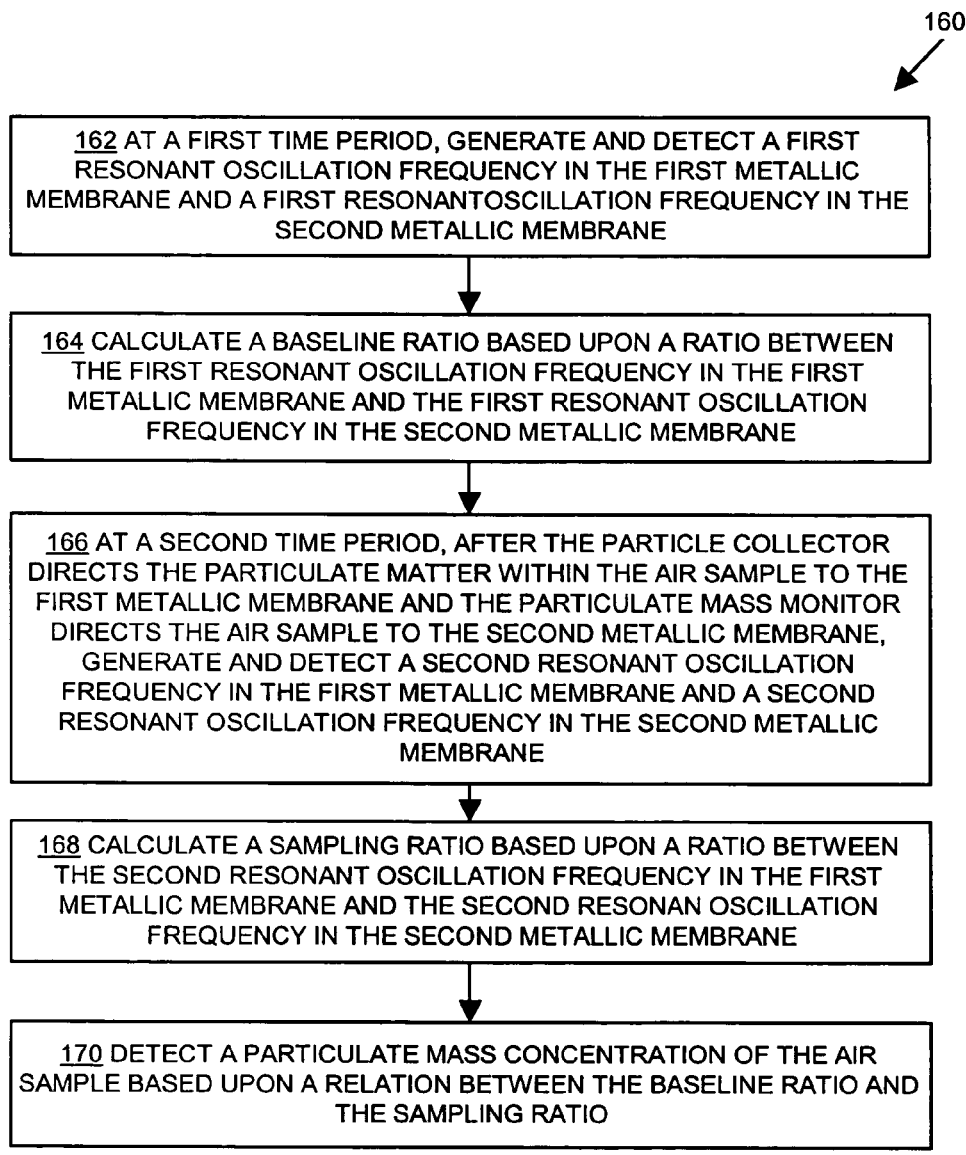
FIG. 9 illustrates a flow chart of a procedure performed by the particulate mass monitor of FIG. 8, according to one embodiment of the invention.

FIG. 9 is a flow chart 160 of a procedure performed by the particulate mass monitor 20 illustrated in FIG. 8. During the procedure, the controller 40 compares the resonant oscillation frequencies of the first metallic membrane 36-1 and the second metallic membrane 36-2 both before and after the particle collector 38 directs the particulate matter 44 to the first metallic membrane 36-1. Such comparison minimizes or eliminates the effect that a variance in the temperature of the air sample 42 has on the air sample mass concentration measurements made by the particulate mass monitor 20 over time.

In step 162, the controller 40 at a first time period, generates and detects a first resonant oscillation frequency in the first metallic membrane 36-1 and a first resonant oscillation frequency in the second metallic membrane 36-2. For example, the controller 40 generates a resonant oscillation frequency in the first metallic membrane 36-1 and in the second metallic membrane 36-2. In such an arrangement, the controller 40 utilizes a first oscillation element 46-1 and first detector element 48-1 to iteratively generate and detect a resonant oscillation frequency within the first metallic membranes 36-1 until the oscillation frequency of the first metallic membranes 36-1 reaches the resonant frequencies of the metallic membrane 36-1. Additionally, the controller 40 utilizes a second oscillation element 46-2 and second detector element 48-2 to iteratively generate and detect an oscillation frequency within the second metallic membranes 36-2 until the oscillation frequency of the second metallic membranes 36-2 reaches the resonant frequencies of the second metallic membrane 36-2.

In step 164, the controller 40 calculates a baseline ratio based upon a ratio between the first resonant oscillation frequency in the first metallic membrane 36-1 and the first resonant oscillation frequency in the second metallic membrane 36-2. For example, as indicated above, an initial ratio of the first and second resonant oscillation frequencies $R_0$ is given as:

$$R_0 = f_{0m}/f_{0r}$$

where $f_{0m}$ is the initial or tare resonant frequency of the first metallic membrane 36-1 and $f_{0r}$ is the initial resonant frequency of the second metallic membrane 36-2.

In step 166, the controller 40 at a second time period, after the particle collector 38 directs the particulate matter 44 within the air sample 42 to the first metallic membrane 36-1 and the particulate mass monitor 20 directs the air sample 144 to the second metallic membrane 36-2, generates and detects a second resonant oscillation frequency in the first metallic membrane 36-1 and a second resonant oscillation frequency in the second metallic membrane 36-2. For example, during operation, the particle collector 38, such as an electrostatic discharge device, produces a corona discharge to electrically charge particulate matter 44 within the air sample 42 (i.e., the air sample oriented in the vicinity of the electrostatic discharge device). The charged particulate matter 44 travels toward, and adheres to, the metallic membrane 36. The corona discharge also creates an airflow 144 directed from the electrostatic precipitation device 38 towards the metallic membrane 36, as caused by an ion wind effect. With the electrically charged particulate matter 44 collected by the first metallic membrane 36-1, the electrostatic discharge device provides the air sample to the second metallic membrane 36-2 where the air sample 144 is substantially free of particulate matter.

The controller 40 utilizes the first oscillation element 46-1 and first detector element 48-1 to iteratively generate and detect a second oscillation frequency within the first metallic membrane 36-1 until the oscillation frequency of the first metallic membrane 36-1 reaches the resonant frequencies of the metallic membrane 36-1. Additionally, the controller 40 utilizes a second oscillation element 46-2 and second detector element 48-2 to iteratively generate and detect an oscillation frequency within the second metallic membranes 36-2 until the oscillation frequency of the second metallic membranes 36-2 reaches the resonant frequencies of the second metallic membrane 36-2.

In step 168, the controller 40 calculates a sampling ratio based upon a ratio between the second resonant oscillation frequency in the first metallic membrane 36-1 and the second resonant oscillation frequency in the second metallic membrane 36-2. For example, the controller 40 (e.g., a computer processor associated with the controller 40) calculates the sampling ratio using the equation:

$$R_f = f_{fm}/f_{fr}$$

where $f_{fm}$ and $f_{fr}$ are the second resonant frequencies of the metallic membranes 36-1, 36-2 of the mass sensing stage 140 and the reference stage 142, respectively, after particle collection has occurred on the first metallic membranes 36-1 in the first stage 140.

In step 170, the controller 40 detects a particulate mass concentration of the air sample 42 based upon a relation between the baseline ratio and the sampling ratio. For example, the controller 40 detects or calculates the particulate mass concentration of the air sample 42 using the equation:

$$\Delta m = m_0[(R_0/R_f)^2 - 1]$$

where $\Delta m$ is based upon a ratio between $R_0$ and $R_f$, the relative resonant oscillation frequencies of the first 36-1 and second 36-2 metallic membranes. Any drifting or change in the resonant frequencies of the first metallic membrane 36-1 and the second metallic membrane 36-2 as caused by changes in temperature, air density, or gravity, for example, are minimized or eliminated because the changes affect equally both $R_0$ and $R_f$.

In one arrangement, the particulate mass monitor 20 includes a membrane transporter 45 coupled to the metallic membrane 36. The membrane transporter 45 is configured to advance the metallic membrane 36 relative to the particle collector 38 such that a clean or unused metallic membrane 36 orients relative to the particle collector 38 prior to the particulate mass monitor 20 measuring the particulate mass concentration of the air sample 42. In one arrangement, the membrane transporter 45 advances the metallic membrane 36 in a substantially automated manner, thereby minimizing the necessity for manual replacement of the metallic membrane over time and allowing for long term, unattended operation of the particulate mass monitor 20.

Figure 10:
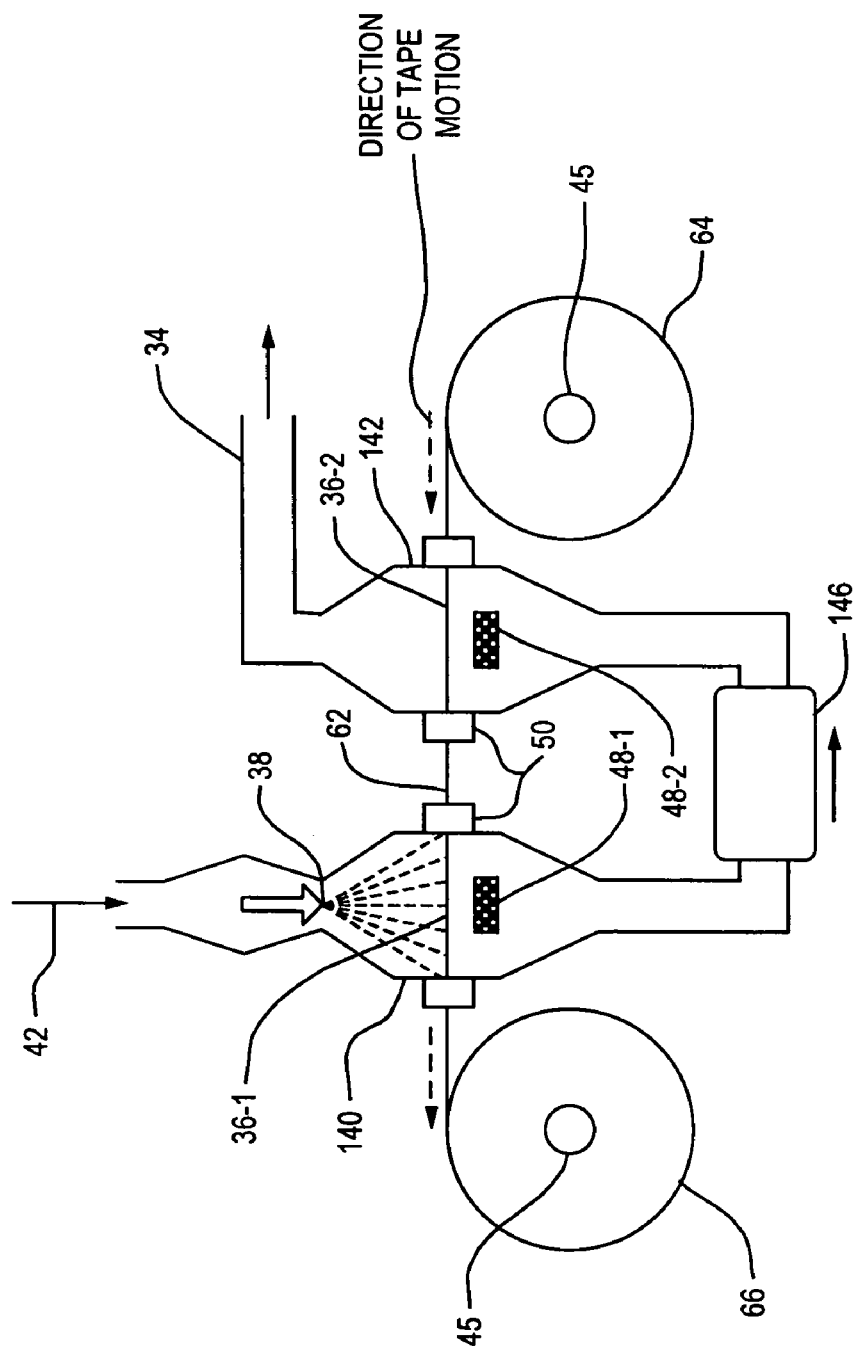
FIG. 10 illustrates a metallic membrane and membrane transporter of the particulate mass monitor of FIGS. 1 and 8.

FIG. 10, for example, illustrates an arrangement of the membrane transporter 45 and metallic membrane 36 where the particulate mass monitor 20 includes two sensing stages 140, 142 as in FIG. 8. As shown, the metallic membrane 36 is configured as a metallic membrane tape 62. The membrane transporter 45 advances the metallic membrane tape 62 from a source (i.e., source roll) 64 to a destination (i.e., destination roll) 66. During operation, the membrane transporter 45 advances the metallic membrane 36 within the particulate mass monitor 20 such that a first metallic membrane portion 36-1 orients in proximity to the particle collector 38 at the mass sensing stage 140 and membrane portion 36-2 at the reference sensing stage 142.

During operation, the controller 40 compares the resonant oscillation frequencies of the first metallic membrane portion 36-1 and the second metallic membrane portion 36-2 both before and after the particle collector 38 directs the particulate matter 44 to the first membrane portion 36-1. Such comparison minimizes or eliminates the effect that a variance in temperature of the air sample 42 has on the air sample mass concentration measurements made by the particulate monitor 20 over time. The same theory described above for the configuration of FIG. 8 applies to the configuration of FIG. 10.

As shown in FIG. 10, the membrane transporter 45 adjusts a position of the metallic membrane tape 62 relative to the particle collector 38 such that the first metallic membrane portion 36-1 is configured to receive particulate matter 44 from the particle collector 38 during a first test.

After a given period of time, or after exposure to a relatively large amount of particulate matter 44, the first metallic membrane portion 36-1 becomes saturated with particulate matter 44. Such saturation can affect the particulate mass measurements made by the particulate mass monitor 20, as a limited amount of particular matter 44 can be collected on the first metallic membrane portion 36-1. The membrane transporter 45, therefore, is configured to advance the metallic membrane 36 within the particulate mass monitor 20 such that a second metallic membrane portion 36-2 orients in proximity to (e.g., becomes aligned with) the particle collector 38 during a second particulate mass monitor test. The membrane transporter 45 advances a "clean" or unused portion of the metallic membrane tape 62 relative to the particle collector 38, thereby allowing the metallic membrane tape to receive a maximal amount of particulate matter 44 from the particle collector 38. Correspondingly, a new clean portion of the metallic membrane tape moves to the reference sensing stage to provide the new reference resonant oscillation frequency against which the resonant oscillation frequency of the mass sensing stage is compared to compensate for any temperature effects. As such, the membrane transporter 45 acts to maintain the measurement accuracy of the particulate mass monitor 20 over time.

In one arrangement, the particulate mass monitor 20 includes a tensioning mechanism 50 configured to generate the tension 47 within the metallic membrane 36 relative to a substantially planar surface defined by the metallic membrane. For example, as shown in FIG. 10, the membrane transporter 45 includes the tensioning mechanism 50. During operation, the membrane transporter 45 applies the tensioning mechanism 50 to the first metallic membrane portion 36-1 and the second metallic membrane portion 36-2 to generate a tension within the portions 36-2, 36-2. In one arrangement, the membrane transporter 45 utilizes a sensor (not shown) coupled to the controller 40 to adjust the tension of the portions 36-1, 36-2 (e.g., to obtain a specific resonant frequency of the metallic membrane portions 36-1, 36-2).

Figure 11:
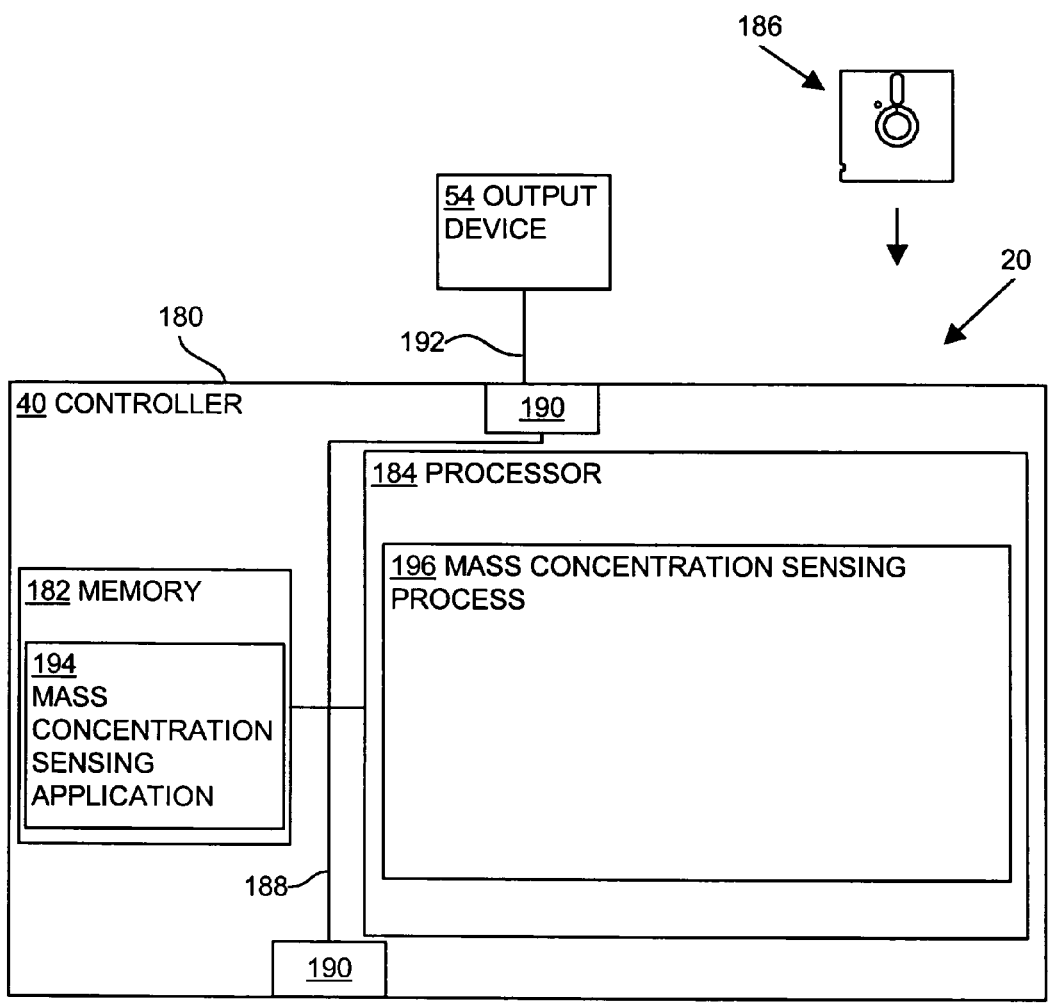
FIG. 11 illustrates an arrangement of a particulate mass monitor, according to one embodiment of the invention.

FIG. 11 illustrates a more detailed architecture of a particulate mass monitor 20 configured as a computerized device 180. The computerized device 180 includes the controller 40 formed of a memory 182 and a processor 184. A computer program product 186 includes an application or logic instructions that are loaded into the computer device 180 to configure the device 180 to perform as a particulate mass monitor 20.

The particulate mass monitor 20, in this example, includes an interconnection mechanism 188 such as a data bus and/or other circuitry that interconnects the controller memory 182 and the processor 184, and one or more communications interfaces 190. The communication interface 188 connects with the output device 54 via connections 192.

The memory 182 may be any type of volatile or non-volatile memory or storage system such as computer memory (e.g., random access memory (RAM), read-only memory (ROM), or other electronic memory), disk memory (e.g., hard disk, floppy disk, optical disk and so forth). The memory 182 is encoded with logic instructions (e.g., software code) and/or data that form a mass concentration sensing application 194 configured according to embodiments of the invention. In other words, the mass concentration sensing application 194 represents software code, instructions and/or data that represent or convey the processing logic steps and operations as explained herein and that reside within memory or storage or within any computer readable medium accessible to the particulate mass monitor 20.

The processor 184 represents any type of circuitry or processing device such as a central processing unit, microprocessor, application-specific integrated circuit, programmable gate array, or other circuitry that can access the mass concentration sensing application 194 encoded within the memory 182 over the interconnection mechanism 188 in order to execute, run, interpret, operate or otherwise perform the mass concentration sensing application 194 logic instructions. Doing so forms the mass concentration sensing process 196. In other words, the mass concentration sensing process 196 represents one or more portions of the logic instructions of the content portion reception application while being executed or otherwise performed on, by, or in the processor 184 within the particulate mass monitor 20. The particulate mass monitor 20 in FIG. 1 collectively represents either one or both of the mass concentration sensing application 194 and the mass concentration sensing process 196.

While this invention has been particularly shown and described with references to preferred embodiments thereof, it will be understood by those skilled in the art that various changes in form and details may be made therein without departing from the spirit and scope of the invention as defined by the appended claims.

For example, in one arrangement described above, the controller 40 is configured to induce, as the first oscillation frequency 70, a fundamental resonant oscillation frequency in the metallic membrane 36. The resonant frequency is defined as the natural oscillation of a mechanical system (e.g., the metallic membrane 36) proportional to the square root of the ratio of the system stiffness constant (e.g., a metallic membrane stiffness constant) and the system mass (e.g., a metallic membrane mass). Such description is by way of example only. In one arrangement the controller 40 is configured to generate a modal oscillation frequency in the metallic membrane 36 where the modal oscillation frequency is based upon a fundamental resonant oscillation frequency of the metallic membrane 36.

FIG. 12 illustrates oscillations nodes associated with the resonant oscillation of the metallic membrane 36. FIGS. 12B–12L illustrate oscillation nodes associated with oscillation of the metallic membrane 36 at modes higher than the fundamental resonant oscillation frequency. The higher modes of resonant oscillation are not harmonically related to the fundamental resonant frequency of the metallic membrane 36. In FIG. 12A where the metallic membrane oscillates at the fundamental resonant frequency, the nodal line (i.e., static line) 200 associated with the oscillation is the circular periphery of the metallic membrane 36. Oscillation at higher modes, as illustrated in FIGS. 12B through 12L, involves further diametrical and/or circular (i.e., concentric) nodes in addition to the peripheral node. By oscillating the metallic membrane 36 at higher resonance modes, the controller 40 increases the sensitivity and accuracy of the particulate mass measurement of the air sample 42 (i.e., the higher resonance modes produce a larger change in frequency in the metallic membrane 36 for a given mass increment).

The metallic membrane 36 has substantially uniform material properties throughout and, when placed under tension, substantially maintains the tensile load 47 over time. Because of the material and mechanical properties of the metallic membrane 36, when the controller 40 provides a modal resonant oscillation frequency input signal to the metallic membrane 36, the metallic membrane 36 responds by providing a modal resonance oscillation output that substantially corresponds to the input signal.

As indicated above, in one arrangement, the particulate mass monitor 20 includes a membrane transporter 45 coupled to the metallic membrane 36. As illustrated in FIG. 10, the metallic membrane 36 is configured as a metallic membrane tape 62. During operation, the membrane transporter 45 advances the metallic tape 62 relative to the particle collector 38 such that, at a certain time, a clean or unused portion of the metallic membrane tape 62 orients relative to the particle collector 38. Such description is by way of example only. In one arrangement, the metallic membrane 36 is configured as a pre-tensioned cartridge. In such a configuration, the membrane transporter 45 advances multiple cartridges within the particulate mass monitor 20 relative to the particle collector 38. The membrane transporter 45, therefore, provides clean or unused cartridges relative to the particle collector 38 over certain time intervals.

As described above with reference to FIG. 10, the metallic membrane 36 is configured as a metallic membrane tape 62 where the membrane transporter 45 advances the metallic membrane tape 62 from a source (i.e., source roll) 64 to a destination (i.e., destination roll) 66. Such description is by way of example only. In another arrangement, the metallic membrane 36 is configured as magazine of pre-tensioned metallic membrane cartridges. During operation, the membrane transporter 45 advances individual magazine cartridges within the particulate mass monitor 20, relative to the particle collector 38, during testing.

What is claimed is:

1. A particulate mass monitor comprising:
   a metallic membrane;
   a particle collector oriented in proximity to the metallic membrane, the particle collector configured to direct particulate matter within an air sample to the metallic membrane;
   a controller in electrical communication with the metallic membrane, the controller configured to generate and detect a resonant oscillation frequency in the metallic membrane, the resonant oscillation frequency of the metallic membrane based upon the particulate matter collected by the metallic membrane; and
   wherein the particle collector comprises a jet impactor configured to direct the particulate matter to the metallic membrane.

2. The particulate mass monitor of claim 1 wherein the controller is configured to:
   at a first time period, generate and detect a first resonant oscillation frequency in the metallic membrane;
   at a second time period, when the particle collector directs the particulate matter within the air sample to the metallic membrane, generate and detect a second resonant oscillation frequency in the metallic membrane; and
   calculate a particulate mass concentration of the air sample based upon a relation between the first resonant oscillation frequency and the second resonant oscillation frequency.

3. The particulate mass monitor of claim 2 wherein:
   at the first time period, the controller is configured to generate and detect the first resonant oscillation frequency in the metallic membrane prior to the particle collector directing the particulate matter to the metallic membrane; and
   at the second time period, the controller is configured to generate and detect the second resonant oscillation frequency in the metallic membrane after the particle collector directs the particulate matter to the metallic membrane.

4. The particulate mass monitor of claim 2 wherein:
   at the first time period, the controller is configured to generate and detect the first resonant oscillation frequency in the metallic membrane while the particle collector directs the particulate matter to the metallic membrane; and
   at the second time period, the controller is configured to generate and detect the second resonant oscillation frequency in the metallic membrane while the particle collector continues to direct the particulate matter to the metallic membrane.

5. The particulate mass monitor of claim 1 wherein the particle collector comprises an electrostatic discharge element oriented in proximity to the metallic membrane, the electrostatic discharge element configured to electrically charge the particulate matter within the air sample.

6. The particulate mass monitor of claim 5 wherein the electrostatic discharge element is configured to ionize air molecules within the air sample to create an ion wind effect enhancing a flow of the air sample through the particulate mass monitor.

7. The particulate mass monitor of claim 1 wherein the controller comprises a capacitive driver in electrical communication with the metallic membrane and a conductive plate, the conductive plate defining a substantially planar surface oriented in proximity and substantially parallel to a substantially planar surface defined by the metallic membrane, the capacitive driver configured to generate an oscillation frequency in the metallic membrane.

8. The particulate mass monitor of claim 7 wherein the controller comprises a capacitive charge detector in electrical communication with one of the metallic membrane and the conductive plate, the capacitive charge detector configured to detect the resonant oscillation frequency in the metallic membrane.

9. The particulate mass monitor of claim 1 wherein the controller comprises a mechanical oscillator coupled to the metallic membrane, the mechanical oscillator configured to generate the resonant oscillation frequency in the metallic membrane.

10. The particulate mass monitor of claim 9 wherein the controller comprises a microphone acoustically coupled with the metallic membrane, the microphone configured to detect the resonant oscillation frequency in the metallic membrane.

11. The particulate mass monitor of claim 1 wherein the controller is configured to generate a fundamental resonant oscillation frequency in the metallic membrane.

12. The particulate mass monitor of claim 11 wherein the controller is configured to generate a modal oscillation frequency in the metallic membrane, the modal oscillation frequency based upon a multiple of the fundamental resonant oscillation frequency of the metallic membrane.

13. The particulate mass monitor of claim 1 comprising a membrane transporter coupled to the metallic membrane, the membrane transporter configured to advance the metallic membrane relative to the particle collector such that a first metallic membrane portion orients in proximity to the particle collector during a first particulate mass monitor test and a second metallic membrane portion orients in proximity to the particle collector during a second particulate mass monitor test.

14. The particulate mass monitor of claim 1 comprising a membrane tensioning device coupled to the metallic membrane, the membrane tensioning device configured to generate a tension within the metallic membrane relative to a substantially planar surface defined by the metallic membrane.

15. The particulate mass monitor of claim 1 further comprising a second metallic membrane, the controller in electrical communication with the second metallic membrane and the controller configured to:
at a first time period, generate and detect a first resonant oscillation frequency in the metallic membrane and a first resonant oscillation frequency in the second metallic membrane;
calculate a baseline ratio based upon a ratio between the first resonant oscillation frequency in the metallic membrane and the first resonant oscillation frequency in the second metallic membrane;
at a second time period, after the particle collector directs the particulate matter within the air sample to the metallic membrane and the particulate mass monitor directs the air sample to the second metallic membrane, generate and detect a second resonant oscillation frequency in the metallic membrane and a second resonant oscillation frequency in the second metallic membrane;
calculate a sampling ratio based upon a ratio between the second resonant oscillation frequency in the metallic membrane and the second resonant oscillation frequency in the second metallic membrane; and
detect a particulate mass concentration of the air sample based upon a relation between the baseline ratio and the sampling ratio.

16. In a particulate mass monitor, a method for monitoring a mass concentration of particulate matter within an air sample comprising:
at a first time period, generating and detecting a first resonant oscillation frequency in a metallic membrane;
directing particulate matter within an air sample to the metallic membrane;
at a second time period, generating and detecting a second resonant oscillation frequency in the metallic membrane;
calculating a particulate mass concentration of the air sample based upon a relation between the first resonant oscillation frequency and the second resonant oscillation frequency; and
wherein directing particulate matter includes impacting the particulate matter onto the metallic membrane via a jet impactor that increases a respective velocity of the particulate matter towards the metallic membrane.

17. The method of claim 16 wherein directing comprises electrically charging the particulate matter within the air sample to deliver the particulate matter within the air sample to the metallic membrane.

18. The method of claim 17 comprising ionizing air molecules within the air sample to create an ion wind effect that causes the air sample to flow relative to the particulate mass monitor.

19. The method of claim 16 comprising advancing the metallic membrane relative to a particle collector such that a first metallic membrane portion orients in proximity to the particle collector during a first particulate mass monitor test and a second metallic membrane portion orients in proximity to the particle collector during a second particulate mass monitor test.

20. The method of claim 16 wherein:
at a first time period, the step of generating and detecting a first resonant oscillation frequency comprises generating and detecting a first resonant oscillation frequency in the metallic membrane and a first resonant oscillation frequency in a second metallic membrane;
calculating a baseline ratio based upon a ratio between the first resonant oscillation frequency in the metallic membrane and the first resonant oscillation frequency in the second metallic membrane;
the step of directing comprises directing the particulate matter within the air sample to the metallic membrane and directing the air sample to the second metallic membrane;
at a second time period, the step of generating and detecting comprises generating and detecting a second resonant oscillation frequency in the metallic membrane and a second resonant oscillation frequency in the second metallic membrane; and
calculating a sampling ratio based upon a ratio between the second resonant oscillation frequency in the metallic membrane and the second resonant oscillation frequency in the second metallic membrane; and
detecting a particulate mass concentration of the air sample based upon a relation between the baseline ratio and the sampling ratio.

21. A computer program product having a computer-readable medium including computer program logic encoded thereon that, when performed on a controller provides a method for performing the operations of:
at a first time period, generating and detecting a first resonant oscillation frequency in a metallic membrane;
at a second time period, after a particle collector impacts particulate matter within an air sample onto the metallic membrane, generating and detecting a second resonant oscillation frequency in the metallic membrane; and
calculating a particulate mass concentration of the air sample based upon a relation between the first resonant oscillation frequency and the second resonant oscillation frequency.

22. The particulate mass monitor as in claim 6, wherein the electrostatic discharge element is positioned upstream with respect to the membrane and a respective flow of the air sample through the particulate mass monitor.

23. The particulate mass monitor as in claim 6, wherein the electrostatic discharge element is a sharp metallic point;
wherein the sharp metallic point is a first electric potential; and
wherein the metallic membrane is set to a second electric potential.

24. The particulate mass monitor as in claim 1, wherein the jet impactor includes a nozzle of decreasing diameter in a path of a flow of the air sample to increase a rate of flow of the air sample towards the metallic membrane.

25. The particulate mass monitor as in claim 24, wherein the metallic membrane includes an adhesive coating to enhance retention of particles in the air sample to the metallic membrane.

26. The particulate mass monitor as in claim 24 further comprising:
an electrostatic device disposed in a path of the air sample to ionize at least a portion of the air sample and create an ion wind, the ion wind enhancing a flow of the air sample towards the metallic membrane.

27. The particulate mass monitor as in claim 1 further comprising:
- a cascade impactor including a series of consecutive impaction stages, a respective at least one nozzle at each consecutive impaction stage have decreasing openings resulting in correspondingly increasing air velocities, and
- the cascade impactor enabling separation of particulate matter in the air sample by size to provide a measurement of particle size distribution of particulate matter in the air sample.

28. The particulate mass monitor as in claim 7, wherein the capacitive driver is configured as a variable frequency oscillator that applies an alternating electrical signal to a combination of the metallic membrane and the conductive plate to create a corresponding periodic deflection in the metallic membrane.

29. The particulate mass monitor as in claim 1, wherein the controller is configured to initiate an ionic wind to enhance flow of the air sample through the particulate mass monitor to collect the particulate matter and, in an absence of the ionic wind, detect the resonant oscillation frequency associated with the metallic membrane to identify collected particulate matter from the air sample.

30. The particulate mass monitor as in claim 1, wherein the jet impactor includes a tapered portion of a respective chamber associated with the particulate mass monitor to increase a speed of the air sample towards the metallic membrane.

31. The particulate mass monitor as in claim 30 further comprising:
- a respective chamber for channeling the air sample through the particulate mass monitor;
- the tapered portion of the respective chamber being disposed between the particle collector in the respective chamber and the metallic membrane in the respective chamber; and
- wherein the controller is configured to activate the particle collector to initiate an ionic wind to enhance flow of the air sample through the respective chamber of the particulate mass monitor to collect the particulate matter and, in an absence of the ionic wind, detect the resonant oscillation frequency associated with the metallic membrane to identify collected particulate matter from the air sample.

32. The particulate mass monitor as in claim 1, wherein metallic membrane is a first metallic membrane disposed in a respective chamber of the particulate mass monitor as a first mass sensing stage, the particulate mass monitor further including:
- a second metallic membrane disposed in the respective chamber as a second mass sensing stage; and
- a barrier disposed in the respective chamber to provide acoustical isolation between the first metallic membrane and the second metallic membrane.

33. The particulate mass monitor as in claim 32, wherein the barrier is a particle filter to minimize a presence of particulate matter within the air sample.

* * * * *